US012611302B2

(12) United States Patent
Miyashiro

(10) Patent No.: US 12,611,302 B2
(45) Date of Patent: Apr. 28, 2026

(54) PROSTHETIC HEART VALVE DEVICE AND ASSOCIATED SYSTEMS AND METHODS

(71) Applicant: TWELVE, INC., Redwood City, CA (US)

(72) Inventor: Katherine Miyashiro, San Francisco, CA (US)

(73) Assignee: Twelve, Inc., Redwood City, CA (US)

( * ) Notice: Subject to any disclaimer, the term of this patent is extended or adjusted under 35 U.S.C. 154(b) by 320 days.

(21) Appl. No.: 18/300,036

(22) Filed: Apr. 13, 2023

(65) Prior Publication Data

US 2023/0248515 A1     Aug. 10, 2023

Related U.S. Application Data

(60) Continuation of application No. 16/904,250, filed on Jun. 17, 2020, now Pat. No. 11,654,021, which is a (Continued)

(51) Int. Cl.
| | |
|---|---|
| *A61F 2/24* | (2006.01) |
| *A61F 2/95* | (2013.01) |
| *A61F 2/966* | (2013.01) |

(52) U.S. Cl.
CPC ............ *A61F 2/2418* (2013.01); *A61F 2/243* (2013.01); *A61F 2/2436* (2013.01);

(Continued)

(58) Field of Classification Search
CPC ...... A61F 2/2409; A61F 2/2418; A61F 2/243; A61F 2/2436; A61F 2/95; A61F 2/9522;

(Continued)

(56) References Cited

U.S. PATENT DOCUMENTS

| | | | |
|---|---|---|---|
| 3,229,736 A | 1/1966 | Hallock |
| 3,245,980 A | 4/1966 | Stright |

(Continued)

FOREIGN PATENT DOCUMENTS

| | | |
|---|---|---|
| CN | 1440261 A | 9/2003 |
| CN | 101076290 A | 11/2007 |

(Continued)

OTHER PUBLICATIONS

US 9,265,606 B2, 02/2016, Buchbinder et al. (withdrawn)

(Continued)

*Primary Examiner* — Robert A Lynch
(74) *Attorney, Agent, or Firm* — Medler Ferro Woodhouse & Mills PLLC

(57) ABSTRACT

A prosthetic heart valve device includes a valve support, a prosthetic valve assembly disposed within the valve support, and an anchoring member. The anchoring member includes a base attached to a first region of the valve support, a plurality of arm units projecting laterally outward from the base and inclined in a direction away from the first region in a deployed state, and a fixation structure extending from the arm units. Each arm unit includes a first portion coupled to the base and a second portion coupled to the fixation structure. The fixation structure includes a plurality of struts that define an annular engagement surface configured to press outwardly against a native annulus of a native heart valve. The first portion of each arm unit has a first flexibility greater that a second flexibility of the second portion of each arm unit.

20 Claims, 14 Drawing Sheets

Related U.S. Application Data division of application No. 15/490,047, filed on Apr. 18, 2017, now Pat. No. 10,702,378.

(52) U.S. Cl.
     CPC .............. *A61F 2002/9534* (2013.01); *A61F 2002/9665* (2013.01); *A61F 2220/0008* (2013.01); *A61F 2220/0016* (2013.01); *A61F 2230/0034* (2013.01); *A61F 2230/005* (2013.01); *A61F 2230/0052* (2013.01); *A61F 2230/0054* (2013.01); *A61F 2230/0067* (2013.01); *A61F 2250/0039* (2013.01); *A61F 2250/0069* (2013.01); *A61F 2250/0096* (2013.01)

(58) Field of Classification Search
     CPC ...... A61F 2002/9505; A61F 2002/9534; A61F 2002/9665; A61F 2220/0008; A61F 2220/0016; A61F 2230/0034; A61F 2230/005; A61F 2230/0052; A61F 2230/0054; A61F 2230/0067; A61F 2250/0039; A61F 2250/0069; A61F 2250/0096
     See application file for complete search history.

(56)                References Cited

U.S. PATENT DOCUMENTS

| | | |
|---|---|---|
| 3,250,154 A | 5/1966 | Breuning |
| 3,256,077 A | 6/1966 | Abler |
| 3,258,883 A | 7/1966 | Campanaro et al. |
| 3,273,910 A | 9/1966 | Willingshofer et al. |
| 3,526,219 A | 9/1970 | Balamuth |
| 3,565,062 A | 2/1971 | Kuris |
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,388,735 A | 6/1983 | Lonescu et al. |
| 4,423,525 A | 1/1984 | Vallana et al. |
| 4,431,006 A | 2/1984 | Trimmer et al. |
| 4,441,216 A | 4/1984 | Ionescu et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,629,459 A | 12/1986 | Ionescu et al. |
| 4,646,736 A | 3/1987 | Auth |
| 4,653,577 A | 3/1987 | Noda |
| 4,666,442 A | 5/1987 | Arru et al. |
| 4,679,556 A | 7/1987 | Lubock et al. |
| 4,692,139 A | 9/1987 | Stiles |
| 4,747,821 A | 5/1988 | Kensey et al. |
| 4,750,902 A | 6/1988 | Wuchinich et al. |
| 4,758,151 A | 7/1988 | Arru et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,892,540 A | 1/1990 | Vallana |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,960,424 A | 10/1990 | Grooters |
| 4,986,830 A | 1/1991 | Owens et al. |
| 4,990,134 A | 2/1991 | Auth |
| 5,002,567 A | 3/1991 | Bona et al. |
| 5,058,570 A | 10/1991 | Idemoto et al. |
| 5,069,664 A | 12/1991 | Guess et al. |
| 5,076,276 A | 12/1991 | Sakurai et al. |
| 5,084,151 A | 1/1992 | Vallana et al. |
| 5,104,406 A | 4/1992 | Curcio et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,344,442 A | 9/1994 | Deac |
| 5,352,199 A | 10/1994 | Tower |
| 5,356,418 A | 10/1994 | Shturman |
| 5,370,684 A | 12/1994 | Vallana et al. |
| 5,387,247 A | 2/1995 | Vallana et al. |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,662,704 A | 9/1997 | Gross et al. |
| 5,681,336 A | 10/1997 | Clement et al. |
| 5,695,507 A | 12/1997 | Auth et al. |
| 5,713,953 A | 2/1998 | Vallana et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,873,812 A | 2/1999 | Ciana et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |

(56) References Cited

U.S. PATENT DOCUMENTS

| | | |
|---|---|---|
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,220,277 B2 | 5/2007 | Arru et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,574 B2 | 3/2009 | Le et al. |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 7,993,392 B2 | 8/2011 | Righini et al. |
| 8,002,826 B2 | 8/2011 | Seguin |
| 8,006,535 B2 | 8/2011 | Righini et al. |
| 8,034,103 B2 | 10/2011 | Burriesci et al. |
| 8,052,750 B2 | 11/2011 | Tuval et al. |
| 8,057,539 B2 | 11/2011 | Ghione et al. |
| 8,062,355 B2 | 11/2011 | Figulla et al. |
| 8,070,799 B2 | 12/2011 | Righini et al. |
| 8,109,996 B2 | 2/2012 | Stacchino et al. |
| 8,114,154 B2 | 2/2012 | Righini et al. |
| 8,226,711 B2 | 7/2012 | Mortier et al. |
| 8,252,051 B2 | 8/2012 | Chau et al. |
| 8,353,953 B2 | 1/2013 | Giannetti et al. |
| 8,398,704 B2 | 3/2013 | Straubinger et al. |
| 8,403,981 B2 | 3/2013 | Forster et al. |
| 8,403,982 B2 | 3/2013 | Giannetti et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,470,024 B2 | 6/2013 | Ghione et al. |
| 8,475,521 B2 | 7/2013 | Suri et al. |
| 8,486,137 B2 | 7/2013 | Suri et al. |
| 8,496,671 B1 | 7/2013 | Hausen |
| 8,512,252 B2 | 8/2013 | Ludomirsky et al. |
| 8,512,397 B2 | 8/2013 | Rolando et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,539,662 B2 | 9/2013 | Stacchino et al. |
| 8,540,767 B2 | 9/2013 | Zhang |
| 8,540,768 B2 | 9/2013 | Stacchino et al. |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,715,207 B2 | 5/2014 | Righini et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,808,367 B2 | 8/2014 | Suri et al. |
| 8,812,431 B2 | 8/2014 | Voigt et al. |
| 8,828,043 B2 | 9/2014 | Chambers |
| 8,834,563 B2 | 9/2014 | Righini |
| 8,840,661 B2 | 9/2014 | Manasse |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,900,295 B2 | 12/2014 | Migliazza et al. |
| 8,920,492 B2 | 12/2014 | Stacchino et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |

(56)        References Cited

U.S. PATENT DOCUMENTS

| | | | |
|---|---|---|---|
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,329 B2 | 3/2015 | Seguin et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,056,008 B2 | 6/2015 | Righini et al. |
| 9,066,800 B2 | 6/2015 | Clague et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,114,010 B2 | 8/2015 | Gaschino et al. |
| 9,119,713 B2 | 9/2015 | Board et al. |
| 9,125,742 B2 | 9/2015 | Yoganathan et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,138,314 B2 | 9/2015 | Rolando et al. |
| 9,149,207 B2 | 10/2015 | Sauter et al. |
| 9,161,836 B2 | 10/2015 | Rolando et al. |
| 9,168,105 B2 | 10/2015 | Giannetti et al. |
| 9,180,005 B1 | 11/2015 | Lashinski et al. |
| 9,186,249 B2 | 11/2015 | Rolando et al. |
| 9,192,466 B2 | 11/2015 | Kovalsky et al. |
| 9,192,471 B2 | 11/2015 | Bolling |
| 9,198,756 B2 | 12/2015 | Aklog et al. |
| 9,204,819 B2 | 12/2015 | Grunwald et al. |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,248,017 B2 | 2/2016 | Rolando et al. |
| 9,254,192 B2 | 2/2016 | Lutter et al. |
| 9,271,833 B2 | 3/2016 | Kim et al. |
| 9,289,289 B2 | 3/2016 | Rolando et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,207 B2 | 5/2016 | Grunwald et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,105 B2 | 6/2016 | Marchisio et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,421,094 B2 | 8/2016 | Schweich, Jr. et al. |
| 9,433,574 B2 | 9/2016 | Martin et al. |
| 9,480,559 B2 | 11/2016 | Vidlund et al. |
| 9,486,313 B2 | 11/2016 | Stacchino et al. |
| 9,504,835 B2 | 11/2016 | Graindorge |
| 9,554,906 B2 | 1/2017 | Aklog et al. |
| 9,610,159 B2 | 4/2017 | Christianson et al. |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,700,413 B2 | 7/2017 | Ruyra Baliarda et al. |
| 9,730,791 B2 | 8/2017 | Ratz et al. |
| 9,730,792 B2 | 8/2017 | Lutter et al. |
| 9,730,794 B2 | 8/2017 | Carpentier et al. |
| 9,744,036 B2 | 8/2017 | Duffy et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,788,931 B2 | 10/2017 | Giordano et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,981 B2 | 12/2017 | Suri et al. |
| 9,848,983 B2 | 12/2017 | Lashinkski et al. |
| 9,861,477 B2 | 1/2018 | Backus et al. |
| 9,861,480 B2 | 1/2018 | Zakai et al. |
| 9,867,695 B2 | 1/2018 | Stacchino et al. |
| 9,895,221 B2 | 2/2018 | Vidlund et al. |
| 9,895,223 B2 | 2/2018 | Stacchino et al. |
| 9,895,225 B2 | 2/2018 | Rolando et al. |
| 9,918,841 B2 | 3/2018 | Righini et al. |
| 9,974,647 B2 | 5/2018 | Ganesan et al. |
| 10,058,313 B2 | 8/2018 | Manasse |
| 10,065,032 B2 | 9/2018 | Ollivier |
| 10,080,659 B1 | 9/2018 | Zentgraf et al. |
| 10,085,835 B2 | 10/2018 | Thambar et al. |
| 10,098,733 B2 | 10/2018 | Righini |
| 10,117,741 B2 | 11/2018 | Schweich, Jr. et al. |
| 10,123,874 B2 | 11/2018 | Khairkhahan et al. |
| 10,143,550 B2 | 12/2018 | Achiluzzi |
| 10,213,301 B2 | 2/2019 | Ganesan et al. |
| 10,245,141 B2 | 4/2019 | Ghione et al. |
| 10,265,166 B2 | 4/2019 | Schweich, Jr. et al. |
| 10,285,810 B2 | 5/2019 | Schweich, Jr. et al. |
| 10,449,039 B2 | 10/2019 | Ganesan et al. |
| 10,702,378 B2 * | 7/2020 | Miyashiro ............... A61F 2/243 |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2002/0188350 A1 | 12/2002 | Arru et al. |
| 2003/0078653 A1 | 4/2003 | Vesely |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |

(56)         References Cited

U.S. PATENT DOCUMENTS

| | | |
|---|---|---|
| 2005/0075720 A1 | 4/2005 | Nguyen et al. |
| 2005/0075727 A1 | 4/2005 | Wheatley |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0228477 A1 | 10/2005 | Grainer et al. |
| 2005/0267523 A1 | 12/2005 | Devellian et al. |
| 2005/0273135 A1 | 12/2005 | Chanduszko |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spencer et al. |
| 2007/0061010 A1 | 3/2007 | Hauser et al. |
| 2007/0073391 A1 | 3/2007 | Bourang et al. |
| 2007/0078302 A1 | 4/2007 | Ortiz et al. |
| 2007/0088431 A1 | 4/2007 | Bourang et al. |
| 2007/0142906 A1 | 6/2007 | Figulla et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0147181 A1 | 6/2008 | Ghione et al. |
| 2008/0161911 A1 | 7/2008 | Lemmon et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2008/0262603 A1 | 10/2008 | Giaquinta et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0105794 A1 | 4/2009 | Ziamo et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023115 A1 | 1/2010 | Robaina et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0063586 A1 | 3/2010 | Hasenkam et al. |
| 2010/0076376 A1 | 3/2010 | Manasse et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlontnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2012/0303048 A1 | 11/2012 | Manasse |
| 2013/0079873 A1 | 3/2013 | Migliazza et al. |
| 2013/0123915 A1 | 5/2013 | Giannetti et al. |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |

(56)                References Cited

U.S. PATENT DOCUMENTS

| | | |
|---|---|---|
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0338766 A1 | 12/2013 | Hastings et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0200662 A1 | 7/2014 | Eftel et al. |
| 2014/0207011 A1 | 7/2014 | Righini et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |

(56) References Cited

U.S. PATENT DOCUMENTS

| | | |
|---|---|---|
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0015543 A1 | 1/2016 | Perouse et al. |
| 2016/0030171 A1 | 2/2016 | Quijano et al. |
| 2016/0038246 A1 | 2/2016 | Wang et al. |
| 2016/0038280 A1* | 2/2016 | Morriss ................. A61F 2/2436 623/2.18 |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0158415 A1 | 6/2016 | Strasly et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib et al. |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296339 A1 | 10/2017 | Thambar et al. |
| 2017/0319333 A1 | 11/2017 | Tegels et al. |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2018/0161585 A1 | 6/2018 | Ollivier |
| 2018/0214263 A1 | 8/2018 | Rolando et al. |
| 2018/0221147 A1 | 8/2018 | Ganesan et al. |
| 2018/0235753 A1 | 8/2018 | Ganesan et al. |
| 2018/0338832 A1 | 11/2018 | Ganesan et al. |
| 2019/0000618 A1 | 1/2019 | Schweich, Jr. et al. |
| 2019/0029814 A1 | 1/2019 | Schweich, Jr. et al. |
| 2019/0142581 A1 | 5/2019 | Maiso et al. |
| 2019/0183641 A1 | 6/2019 | Ganesan et al. |
| 2019/0192292 A1 | 6/2019 | Schweich, Jr. et al. |

FOREIGN PATENT DOCUMENTS

| | | | |
|---|---|---|---|
| CN | 101291637 | A | 10/2008 |
| CN | 103491900 | A | 1/2014 |
| DE | 19605042 | A1 | 1/1998 |
| DE | 102006052564 | B3 | 12/2007 |
| EP | 186104 | A2 | 7/1986 |
| EP | 0224080 | B1 | 7/1992 |
| EP | 1512383 | A2 | 3/2005 |
| EP | 1088529 | B1 | 6/2005 |
| EP | 1545371 | A2 | 6/2005 |
| EP | 1551274 | A2 | 7/2005 |
| EP | 1629794 | A2 | 3/2006 |
| EP | 1646332 | A2 | 4/2006 |
| EP | 1702247 | A2 | 9/2006 |
| EP | 1734903 | A1 | 12/2006 |
| EP | 1891914 | | 2/2008 |
| EP | 1967164 | A2 | 9/2008 |
| EP | 2026280 | A1 | 2/2009 |
| EP | 2033581 | A1 | 3/2009 |
| EP | 2037829 | A2 | 3/2009 |
| EP | 2081519 | A2 | 7/2009 |
| EP | 2111190 | A2 | 10/2009 |
| EP | 2142143 | A2 | 1/2010 |
| EP | 2167742 | A1 | 3/2010 |
| EP | 2014257 | B1 | 9/2010 |
| EP | 2278944 | A2 | 2/2011 |
| EP | 2033597 | B1 | 3/2011 |
| EP | 2306821 | A1 | 4/2011 |
| EP | 2327429 | A1 | 6/2011 |
| EP | 2165651 | B1 | 8/2011 |
| EP | 1719476 | B1 | 11/2011 |
| EP | 2399527 | A1 | 12/2011 |
| EP | 2400924 | | 1/2012 |
| EP | 2400926 | A2 | 1/2012 |
| EP | 2410947 | A1 | 2/2012 |
| EP | 2416739 | A2 | 2/2012 |
| EP | 2419050 | | 2/2012 |
| EP | 2444031 | A2 | 4/2012 |
| EP | 2488126 | A1 | 8/2012 |
| EP | 2509538 | A2 | 10/2012 |
| EP | 2549955 | A1 | 1/2013 |
| EP | 2549956 | A1 | 1/2013 |
| EP | 2566416 | A1 | 3/2013 |
| EP | 2586492 | A1 | 5/2013 |
| EP | 2618784 | A2 | 7/2013 |
| EP | 2623068 | A1 | 8/2013 |
| EP | 2626013 | A2 | 8/2013 |
| EP | 2629699 | A1 | 8/2013 |
| EP | 2633457 | A1 | 9/2013 |
| EP | 2637659 | A1 | 9/2013 |
| EP | 2641569 | A1 | 9/2013 |
| EP | 2644158 | | 10/2013 |
| EP | 2654624 | A1 | 10/2013 |
| EP | 2656794 | A1 | 10/2013 |

(56)  References Cited

FOREIGN PATENT DOCUMENTS

| | | | |
|---|---|---|---|
| EP | 2656795 | A1 | 10/2013 |
| EP | 2656796 | A1 | 10/2013 |
| EP | 2667823 | A1 | 12/2013 |
| EP | 2670358 | A2 | 12/2013 |
| EP | 2676640 | A1 | 12/2013 |
| EP | 2688041 | A2 | 1/2014 |
| EP | 2695586 | | 2/2014 |
| EP | 2697721 | A2 | 2/2014 |
| EP | 2713953 | A1 | 4/2014 |
| EP | 2714068 | A2 | 4/2014 |
| EP | 2723272 | A2 | 4/2014 |
| EP | 2723273 | A2 | 4/2014 |
| EP | 2723277 | A1 | 4/2014 |
| EP | 2739214 | A2 | 6/2014 |
| EP | 2741711 | A2 | 6/2014 |
| EP | 2750630 | A1 | 7/2014 |
| EP | 2750631 | A1 | 7/2014 |
| EP | 2755562 | A1 | 7/2014 |
| EP | 2755602 | A1 | 7/2014 |
| EP | 2757962 | A1 | 7/2014 |
| EP | 2777616 | A1 | 9/2014 |
| EP | 2777617 | A1 | 9/2014 |
| EP | 2782523 | A1 | 10/2014 |
| EP | 2785282 | A1 | 10/2014 |
| EP | 2786817 | | 10/2014 |
| EP | 2790609 | A1 | 10/2014 |
| EP | 2793751 | A1 | 10/2014 |
| EP | 2229921 | B1 | 11/2014 |
| EP | 2809263 | A2 | 12/2014 |
| EP | 2810620 | A1 | 12/2014 |
| EP | 2814428 | A1 | 12/2014 |
| EP | 2814429 | A1 | 12/2014 |
| EP | 2819617 | A1 | 1/2015 |
| EP | 2819618 | A1 | 1/2015 |
| EP | 2819619 | A1 | 1/2015 |
| EP | 2833836 | A1 | 2/2015 |
| EP | 2838475 | A1 | 2/2015 |
| EP | 2839815 | | 2/2015 |
| EP | 2844190 | | 3/2015 |
| EP | 2849680 | A2 | 3/2015 |
| EP | 2849681 | A1 | 3/2015 |
| EP | 2852354 | A2 | 4/2015 |
| EP | 2861186 | A2 | 4/2015 |
| EP | 2870933 | | 5/2015 |
| EP | 2873011 | A1 | 5/2015 |
| EP | 2875797 | A1 | 5/2015 |
| EP | 2760375 | | 6/2015 |
| EP | 2882374 | A1 | 6/2015 |
| EP | 2886082 | | 6/2015 |
| EP | 2886083 | A1 | 6/2015 |
| EP | 2886084 | A1 | 6/2015 |
| EP | 2895111 | A2 | 7/2015 |
| EP | 2250976 | B1 | 8/2015 |
| EP | 2901966 | A1 | 8/2015 |
| EP | 2907479 | A1 | 8/2015 |
| EP | 2945572 | A1 | 11/2015 |
| EP | 2948094 | A1 | 12/2015 |
| EP | 2948102 | A1 | 12/2015 |
| EP | 2964152 | A1 | 1/2016 |
| EP | 2967859 | A1 | 1/2016 |
| EP | 2967860 | A1 | 1/2016 |
| EP | 2967866 | A2 | 1/2016 |
| EP | 2968847 | A1 | 1/2016 |
| EP | 2981208 | | 2/2016 |
| EP | 2982336 | A1 | 2/2016 |
| EP | 2999433 | A1 | 3/2016 |
| EP | 3003187 | A1 | 4/2016 |
| EP | 3003219 | A1 | 4/2016 |
| EP | 3003220 | A1 | 4/2016 |
| EP | 3010447 | A1 | 4/2016 |
| EP | 3013281 | A1 | 5/2016 |
| EP | 3017792 | A1 | 5/2016 |
| EP | 3021792 | A2 | 5/2016 |
| EP | 3023117 | A1 | 5/2016 |
| EP | 3027143 | A1 | 6/2016 |
| EP | 3033048 | A2 | 6/2016 |
| EP | 3037064 | A1 | 6/2016 |
| EP | 3050541 | A1 | 8/2016 |
| EP | 3079633 | | 10/2016 |
| EP | 3102152 | | 12/2016 |
| EP | 2470119 | B1 | 5/2017 |
| EP | 2999436 | A4 | 5/2017 |
| EP | 3184081 | | 6/2017 |
| EP | 3191027 | | 7/2017 |
| EP | 2611389 | | 8/2017 |
| EP | 3082656 | | 8/2017 |
| EP | 3206628 | | 8/2017 |
| EP | 2010103 | | 9/2017 |
| EP | 3223751 | | 10/2017 |
| EP | 3027144 | | 11/2017 |
| EP | 3110368 | | 11/2017 |
| EP | 3110369 | | 11/2017 |
| EP | 3132773 | | 11/2017 |
| JP | 6504516 | | 5/1994 |
| JP | H10258124 | A | 9/1998 |
| JP | 2002509756 | A | 4/2002 |
| JP | 2005280917 | A | 10/2005 |
| JP | 2008528117 | A | 7/2008 |
| JP | 2008541863 | A | 11/2008 |
| JP | 2009195712 | A | 9/2009 |
| JP | 2010518947 | A | 6/2010 |
| JP | 5219518 | B2 | 6/2013 |
| WO | WO-1992017118 | A1 | 10/1992 |
| WO | WO-1995016407 | A1 | 6/1995 |
| WO | WO-1999004730 | A1 | 2/1999 |
| WO | WO-1999039648 | A1 | 8/1999 |
| WO | WO-1999049799 | A1 | 10/1999 |
| WO | WO-2001010343 | | 2/2001 |
| WO | WO-2002003892 | A1 | 1/2002 |
| WO | WO-2002028421 | A1 | 4/2002 |
| WO | WO-2002039908 | A2 | 5/2002 |
| WO | WO-2003043685 | A2 | 5/2003 |
| WO | WO-2004084746 | A2 | 10/2004 |
| WO | WO-2004093728 | A2 | 11/2004 |
| WO | WO-2004096097 | A2 | 11/2004 |
| WO | WO-2004112657 | A1 | 12/2004 |
| WO | WO-2005002466 | A2 | 1/2005 |
| WO | WO-2005007219 | A2 | 1/2005 |
| WO | WO-2005009285 | A2 | 2/2005 |
| WO | WO-2005009506 | A2 | 2/2005 |
| WO | WO-2005087140 | A1 | 9/2005 |
| WO | WO-2006041877 | A2 | 4/2006 |
| WO | WO-2006063199 | A2 | 6/2006 |
| WO | WO-2007008371 | A2 | 1/2007 |
| WO | WO-2007067820 | A2 | 6/2007 |
| WO | WO-2007098232 | | 8/2007 |
| WO | WO-2008022077 | A2 | 2/2008 |
| WO | WO-2008028569 | A1 | 3/2008 |
| WO | WO-2008035337 | A2 | 3/2008 |
| WO | WO-2008103497 | A2 | 8/2008 |
| WO | WO-2008103722 | | 8/2008 |
| WO | WO-2008129405 | A2 | 10/2008 |
| WO | WO-2009045338 | A1 | 4/2009 |
| WO | WO-2009091509 | | 7/2009 |
| WO | WO-2010006627 | A1 | 1/2010 |
| WO | WO-2010008549 | A1 | 1/2010 |
| WO | WO-2010057262 | A1 | 5/2010 |
| WO | WO-2010080594 | A2 | 7/2010 |
| WO | WO-2010098857 | A1 | 9/2010 |
| WO | WO-2010099032 | A2 | 9/2010 |
| WO | WO-2010117680 | A1 | 10/2010 |
| WO | WO-2010121076 | | 10/2010 |
| WO | WO-2011025981 | | 3/2011 |
| WO | WO-2011047168 | A1 | 4/2011 |
| WO | WO-2011051043 | A1 | 5/2011 |
| WO | WO-2011057087 | A1 | 5/2011 |
| WO | WO-2011072084 | A2 | 6/2011 |
| WO | WO-2011106137 | A1 | 9/2011 |
| WO | WO-2011106544 | A1 | 9/2011 |
| WO | WO-2011111047 | A2 | 9/2011 |
| WO | WO-2011137531 | A1 | 11/2011 |
| WO | WO-2011139747 | A1 | 11/2011 |
| WO | WO-2012011018 | A1 | 1/2012 |
| WO | WO-2012011108 | A2 | 1/2012 |

(56)          References Cited

FOREIGN PATENT DOCUMENTS

| | | |
|---|---|---|
| WO | WO-2012027487 A2 | 3/2012 |
| WO | WO-2012035279 A1 | 3/2012 |
| WO | WO-2012040655 A2 | 3/2012 |
| WO | WO-2012047644 A2 | 4/2012 |
| WO | WO-2012052718 | 4/2012 |
| WO | WO-2012055498 A1 | 5/2012 |
| WO | WO-2012087842 A1 | 6/2012 |
| WO | WO-2012095455 A2 | 7/2012 |
| WO | WO-2012102928 A1 | 8/2012 |
| WO | WO-2012106602 A2 | 8/2012 |
| WO | WO-2012118508 A1 | 9/2012 |
| WO | WO-2012118816 A1 | 9/2012 |
| WO | WO-2012118894 A2 | 9/2012 |
| WO | WO-2012177942 A2 | 12/2012 |
| WO | WO-2013021374 A2 | 2/2013 |
| WO | WO-2013021375 A2 | 2/2013 |
| WO | WO-2013028387 A2 | 2/2013 |
| WO | WO-2013059743 A1 | 4/2013 |
| WO | WO-2013059747 A1 | 4/2013 |
| WO | WO-2013114214 A2 | 8/2013 |
| WO | WO-2013120181 A1 | 8/2013 |
| WO | WO-2013123059 A1 | 8/2013 |
| WO | WO-2013128432 A1 | 9/2013 |
| WO | WO-2013130641 A1 | 9/2013 |
| WO | WO-2013131925 A1 | 9/2013 |
| WO | WO-2013140318 A1 | 9/2013 |
| WO | WO-2013148017 A1 | 10/2013 |
| WO | WO-2013148018 A1 | 10/2013 |
| WO | WO-2013148019 A1 | 10/2013 |
| WO | WO-2013150512 A1 | 10/2013 |
| WO | WO-2013152161 A1 | 10/2013 |
| WO | WO-2013158613 A1 | 10/2013 |
| WO | WO-2013169448 A1 | 11/2013 |
| WO | WO-2013175468 A2 | 11/2013 |
| WO | WO-2013176583 A2 | 11/2013 |
| WO | WO-2013188077 A1 | 12/2013 |
| WO | WO-2013192107 A1 | 12/2013 |
| WO | WO-2014036113 A1 | 3/2014 |
| WO | WO-2014043527 A2 | 3/2014 |
| WO | WO-2014047111 A1 | 3/2014 |
| WO | WO-2014047325 A1 | 3/2014 |
| WO | WO-2014055981 A1 | 4/2014 |
| WO | WO-2014059432 A2 | 4/2014 |
| WO | WO-2014064694 A2 | 5/2014 |
| WO | WO-2014066365 A1 | 5/2014 |
| WO | WO-2014089424 A1 | 6/2014 |
| WO | WO-2014093861 A1 | 6/2014 |
| WO | WO-2014111918 A1 | 7/2014 |
| WO | WO-2014114794 A2 | 7/2014 |
| WO | WO-2014114795 A1 | 7/2014 |
| WO | WO-2014114796 A1 | 7/2014 |
| WO | WO-2014114798 A1 | 7/2014 |
| WO | WO-2014116502 A1 | 7/2014 |
| WO | WO-2014121280 A2 | 8/2014 |
| WO | WO-2014128705 A1 | 8/2014 |
| WO | WO-2014134277 A1 | 9/2014 |
| WO | WO-2014138194 A1 | 9/2014 |
| WO | WO-2014138284 A1 | 9/2014 |
| WO | WO-2014138482 A1 | 9/2014 |
| WO | WO-2014138868 A1 | 9/2014 |
| WO | WO-2014144100 A2 | 9/2014 |
| WO | WO-2014144937 A2 | 9/2014 |
| WO | WO-2014145338 A1 | 9/2014 |
| WO | WO-2014147336 A1 | 9/2014 |
| WO | WO-2014152306 A1 | 9/2014 |
| WO | WO-2014152375 A2 | 9/2014 |
| WO | WO-2014152503 A1 | 9/2014 |
| WO | WO-2014153544 A1 | 9/2014 |
| WO | WO-2014158617 A1 | 10/2014 |
| WO | WO-2014162181 A2 | 10/2014 |
| WO | WO-2014162306 A2 | 10/2014 |
| WO | WO-2014163705 A1 | 10/2014 |
| WO | WO-2014168655 A1 | 10/2014 |
| WO | WO-2014179391 A2 | 11/2014 |
| WO | WO-2014181336 A1 | 11/2014 |
| WO | WO-2014189974 A1 | 11/2014 |
| WO | WO-2014191994 A1 | 12/2014 |
| WO | WO-2014194178 A1 | 12/2014 |
| WO | WO-2014201384 A1 | 12/2014 |
| WO | WO-2014201452 A1 | 12/2014 |
| WO | WO-2014205064 A1 | 12/2014 |
| WO | WO-2014207699 A1 | 12/2014 |
| WO | WO-2014210124 A1 | 12/2014 |
| WO | WO-2014210299 A1 | 12/2014 |
| WO | WO-2015009503 A2 | 1/2015 |
| WO | WO-2015020971 A1 | 2/2015 |
| WO | WO-2015028986 A1 | 3/2015 |
| WO | WO-2015051430 A1 | 4/2015 |
| WO | WO-2015052663 A1 | 4/2015 |
| WO | WO-2015057407 A1 | 4/2015 |
| WO | WO-2015057735 A1 | 4/2015 |
| WO | WO-2015057995 A2 | 4/2015 |
| WO | WO-2015061378 A1 | 4/2015 |
| WO | WO-2015061431 A1 | 4/2015 |
| WO | WO-2015061463 A1 | 4/2015 |
| WO | WO-2015061533 A1 | 4/2015 |
| WO | WO-2015075128 A1 | 5/2015 |
| WO | WO-2015081775 A1 | 6/2015 |
| WO | WO-2015089334 A1 | 6/2015 |
| WO | WO-2015092554 A2 | 6/2015 |
| WO | WO-2015118464 A1 | 8/2015 |
| WO | WO-2015120122 A2 | 8/2015 |
| WO | WO-2015125024 A2 | 8/2015 |
| WO | WO-2015127264 A1 | 8/2015 |
| WO | WO-2015127283 A1 | 8/2015 |
| WO | WO-2015128739 A2 | 9/2015 |
| WO | WO-2015128741 A2 | 9/2015 |
| WO | WO-2015128747 A2 | 9/2015 |
| WO | WO-2015132667 A1 | 9/2015 |
| WO | WO-2015132668 A1 | 9/2015 |
| WO | WO-2015135050 A1 | 9/2015 |
| WO | WO-2015142648 A1 | 9/2015 |
| WO | WO-2015142834 A1 | 9/2015 |
| WO | WO-2015148241 A1 | 10/2015 |
| WO | WO-2015171190 A1 | 11/2015 |
| WO | WO-2015171743 A2 | 11/2015 |
| WO | WO-2015179181 | 11/2015 |
| WO | WO-2015191604 | 12/2015 |
| WO | WO-2015191839 A1 | 12/2015 |
| WO | WO-2015195823 A1 | 12/2015 |
| WO | WO-2016011185 A1 | 1/2016 |
| WO | WO-2016020918 A1 | 2/2016 |
| WO | WO-2016027272 A1 | 2/2016 |
| WO | WO-2016059533 A1 | 4/2016 |
| WO | WO-2016065158 A1 | 4/2016 |
| WO | WO-2016073741 A1 | 5/2016 |
| WO | WO-2016083551 A1 | 6/2016 |
| WO | WO-2016093877 A1 | 6/2016 |
| WO | WO-2016097337 A1 | 6/2016 |
| WO | WO-2016108181 A1 | 7/2016 |
| WO | WO-2016133950 | 8/2016 |
| WO | WO-2016150806 | 9/2016 |
| WO | WO-2016201024 | 12/2016 |
| WO | WO-2016209970 | 12/2016 |
| WO | WO-2017011697 | 1/2017 |
| WO | WO-2017062640 | 4/2017 |
| WO | WO-2017096157 | 6/2017 |
| WO | WO-2017100927 | 6/2017 |
| WO | WO-2017101232 | 6/2017 |
| WO | WO-2017117388 | 7/2017 |
| WO | WO-2017127939 | 8/2017 |
| WO | WO-2017173331 | 10/2017 |
| WO | WO-2017196511 | 11/2017 |
| WO | WO-2017196909 | 11/2017 |
| WO | WO-2017196977 | 11/2017 |
| WO | WO-2017197064 | 11/2017 |
| WO | WO-2017218671 | 12/2017 |
| WO | WO-2018017886 | 1/2018 |
| WO | WO-2018029680 | 2/2018 |
| WO | WO-2018167536 | 9/2018 |

(56)           References Cited

FOREIGN PATENT DOCUMENTS

| WO | WO-2019069145 | 4/2019 |
| WO | WO-2019209927 | 10/2019 |

OTHER PUBLICATIONS

Bernard et al., "Aortic Valve Area Evolution After Percutaneous Aortic Valvuloplasty," European Heart Journal, Jul. 1990, vol. 11 (2), pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.

Cimino, "Ultrasonic Surgery: Power Quantification and Efficiency Optimization", Aesthetic Surgery Journal, Feb. 2001, pp. 233-241.

Cowell et al., "A Randomized Trial of Intensive Lipid-Lowering Therapy in Calcific Aortic Stenosis," NEJM, Jun. 2005, vol. 352 (23), pp. 2389-2397.

De Korte et al., "Characterization of Plaque Components and Vulnerability with Intravascular Ultrasound Elastography", Phys. Med. Biol., Feb. 2000, vol. 45, pp. 1465-1475.

European Search Report dated Mar. 13, 2015 for European Application. No. 05853460.3.

Feldman, "Restenosis Following Successful Balloon Valvuloplasty: Bone Formation in Aortic Valve Leaflets", Cathet Cardiovasc Diagn, May 1993, vol. 29 (1), pp. 1-7.

Fitzgerald et al., "Intravascular Sonotherapy Decreased Neointimal Hyperplasia After Stent Implantation in Swine", Circulation, Feb. 2001, vol. 103, pp. 1828-1831.

Freeman et al., "Ultrasonic Aortic Valve Decalcification: Serial Doppler Echocardiographic Follow Up", J Am Coll Cardiol., Sep. 1990, vol. 16 (3), pp. 623-630.

Greenleaf et al., "Selected Methods for Imaging Elastic Properties of Biological Tissues", Annu. Rev. Biomed. Eng., Apr. 2003, vol. 5, pp. 57-78.

Gunn et al., "New Developments in Therapeutic Ultrasound-Assisted Coronary Angioplasty", Curr Interv Cardiol Rep., Dec. 1990, vol. 1 (4), pp. 281-290.

Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.

Hallgrimsson et al., "Chronic Non-Rheumatic Aortic Valvular Disease: a Population Study Based on Autopsies", J Chronic Dis., Jun. 1979, vol. 32 (5), pp. 355-363.

International Search Report and Written Opinion dated Sep. 11, 2018 for PCT Application No. PCT/US2018/038841, 15 pages.

International Search Report and Written Opinion dated Sep. 4, 2018 for PCT Application No. PCT/US2018/027966, 17 pages.

International Search Report and Written Opinion dated Jul. 11, 2018 for PCT Application No. PCT/US2018/027990, 15 pages.

International Search Report and Written Opinion dated Jun. 28, 2018 for PCT Application No. PCT/US2018/027983, 15 pages.

International Search Report and Written Opinion dated Aug. 3, 2018 for PCT Application No. PCT/US2018/035086, 15 pages.

International Search Report and Written Opinion dated Aug. 9, 2018 for PCT Application No. PCT/US2018/035081, 11 pages.

International Search Report and Written Opinion dated Sep. 11, 2018 for PCT Application No. PCT/US2018/038847, 18 pages.

Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.

Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.

Mcbride et al "Aortic Valve Decalcification", J Thorac Cardiovas-Surg, Jul. 1990, vol. 100, pp. 36-42.

Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.

Mohler, "Mechanisms of Aortic Valve Calcificaion", Am J Cardiol, Dec. 2004, vol. 94 (11), pp. 1396-1402.

Otto et al., "Three-Year Outcome After Balloon Aortic Valvuloplasty. Insights into Prognosis of Valvular Aortic Stenosis", Circulation, Feb. 1994, vol. 89, pp. 642-650.

Passik et al., "Temporal Changes in the Causes of Aortic Stenosis: A Surgical Pathologic Study of 646 Cases", Mayo Clin Proc, Feb. 1987, vol. 62, pp. 19-123.

Quaden et al., "Percutaneous Aortic Valve Replacement: Resection Before Implantation", Eur J Cardiothorac Surg, Jan. 2005, vol. 27, pp. 836-840.

Riebman et al., "New Concepts in the Management of Patients with Aortic Valve Disease", Abstract, Valvular Heart Disease, JACC, Mar. 2004, p. 34A.

Rosenschein et al., "Percutaneous Transluminal Therapy of Occluded Saphenous Vein Grafts" Circulation, Jan. 1999, vol. 99, pp. 26-29.

Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.

Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp. 643-652.

Search Report and Written Opinion dated Dec. 10, 2012 for PCT Application No. PCT/US2012/043636.

Search Report and Written Opinion dated Dec. 6, 2016 for PCT Application No. PCT/US2016/047831.

Search Report and Written Opinion dated Apr. 19, 2014 PCT Application No. PCT/US2012/061215.

Search Report and Written Opinion dated Apr. 19, 2014 PCT Application No. PCT/US2012/061219.

Search Report and Written Opinion dated Mar. 2, 2015 for PCT Application No. PCT/US2014/029549.

Search Report and Written Opinion dated May 1, 2012 for PCT Application No. PCT/US2011/065627.

Search Report and Written Opinion dated May 22, 2007 for PCT Application No. PCT/US2005/044543.

Search Report and Written Opinion dated Oct. 20, 2014 for PCT Application No. PCT/US2014/038849.

Search Report and Written Opinion dated Sep. 4, 2014 for PCT Application No. PCT/US2014/014704.

The CoreValve System Medtronic, 2012, 4 Pages.

Van Den Brand et al., "Histological Changes in the Aortic Valve after Balloon Dilation: Evidence for a Delayed Healing Process", Br Heart J, Jun. 1992, vol. 67, pp. 445-459.

Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.

Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.

Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.

Wang, "Balloon Aortic Valvuloplasty", Prog Cardiovasc Dis., Jul.-Aug. 1997, vol. 40 (1), pp. 27-36.

Wilson et al., "Elastography—The movement Begins", Phys. Med. Biol., Jun. 2000, vol. 45, pp. 1409-1421.

Yock et al, "Catheter-Based Ultrasound Thrombolysis", Circulation, Mar. 1997, vol. 95 (6), pp. 1411-1416.

Office action, China National Intellectual Property Administration, Appl. No. 2188002618.5, dated May 21, 2021.

* cited by examiner

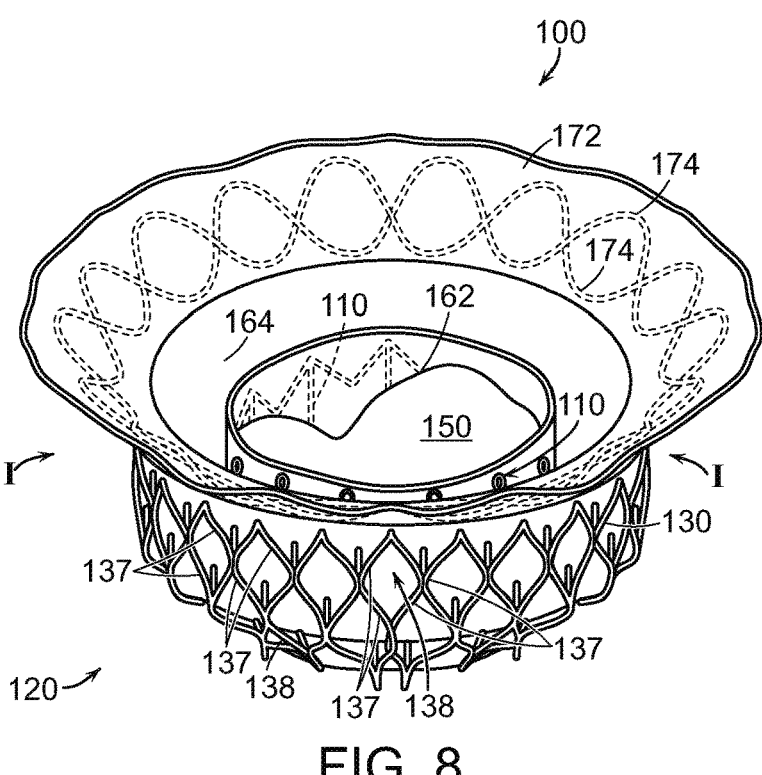
FIG. 8
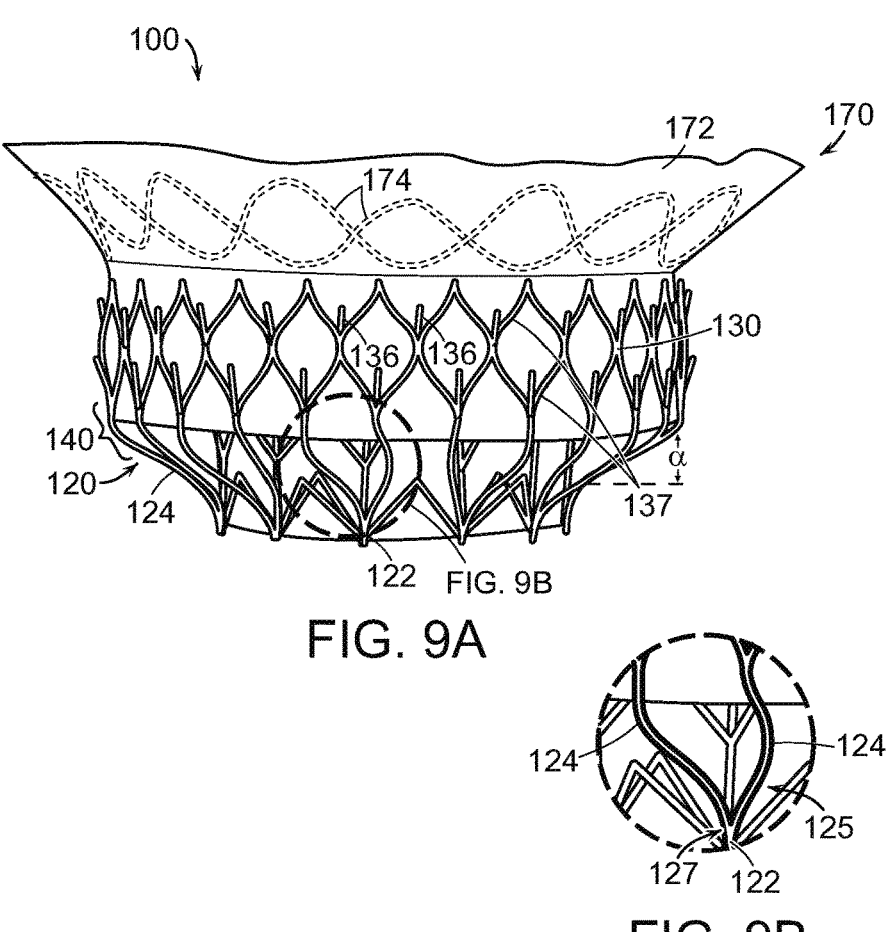
FIG. 9A
FIG. 9B

PROSTHETIC HEART VALVE DEVICE AND ASSOCIATED SYSTEMS AND METHODS

This application is a continuation of U.S. patent application Ser. No. 16/904,250, filed Jun. 17, 2020, which is a divisional of U.S. patent application Ser. No. 15/490,047, filed Apr. 18, 2017, now U.S. Pat. No. 10,703,378, the entire contents of each of which is incorporated herein by reference.

TECHNICAL FIELD

The present technology relates generally to prosthetic heart valve devices. Several embodiments of the present technology are well suited for percutaneous repair and/or replacement of native mitral valves.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up in to the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, CA, USA) and the Edwards-Sapien® Valve from Edwards Lifesciences (Irvine, CA, USA). Both valve systems include an expandable frame and a tri-leaflet bioprosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

BRIEF DESCRIPTION OF THE DRAWINGS

Many aspects of the present disclosure can be better understood with reference to the following drawings. The components in the drawings are not necessarily to scale, and instead emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers and/or letters are used to identify similar or analogous components or features, but the use of the same reference number does not imply that the parts should be construed to be identical. Indeed, in many examples described herein, identically numbered components refer to different embodiments that are distinct in structure and/or function. The headings provided herein are for convenience only.

FIG. 8 is a top isometric view of a prosthetic heart valve device in accordance with an embodiment of the present technology.

FIG. 9A is a side view of the prosthetic heart valve device of FIG. 8, and FIG. 9B is a detailed view of a portion of the prosthetic heart valve device shown in FIG. 9A.

DETAILED DESCRIPTION

Figure 1:
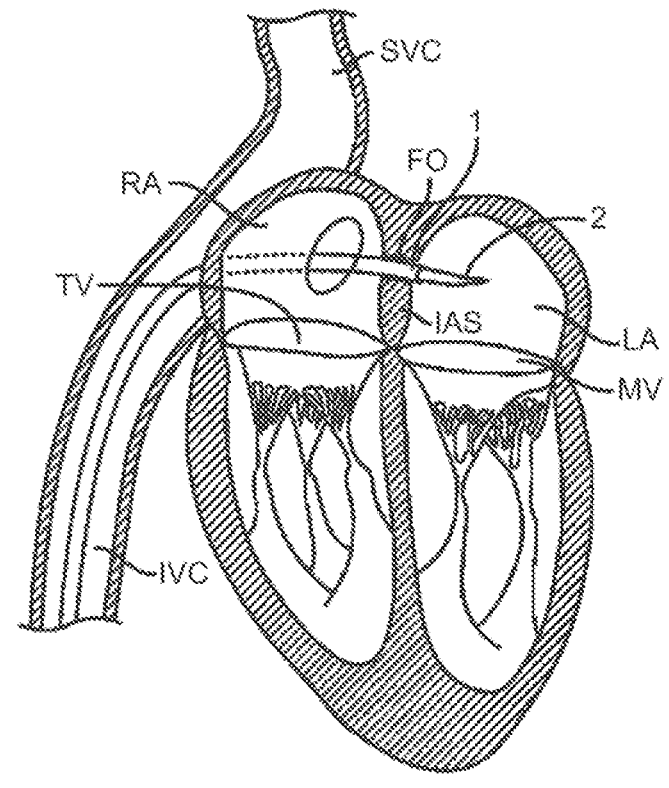
FIG. 1 is a schematic, cross-sectional illustration of the heart showing an antegrade approach to the native mitral valve from the venous vasculature in accordance with various embodiments of the present technology.

Specific details of several embodiments of the technology are described below with reference to FIGS. 1-19. Although many of the embodiments are described below with respect to prosthetic valve devices, systems, and methods for percutaneous replacement of a native mitral valve, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-19.

With regard to the terms "distal" and "proximal" within this description, unless otherwise specified, the terms can reference a relative position of the portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use trileaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

Embodiments of the present technology provide systems, methods and apparatus to treat heart valves of the body, such as the mitral valve, that address the challenges associated with the anatomy of the mitral valve and provide for repositioning and removal of a partially deployed device. The apparatus and methods enable a percutaneous approach using a catheter delivered intravascularly through a vein or artery into the heart, or through a cannula inserted through the heart wall. For example, the apparatus and methods are particularly well-suited for trans-septal approaches, but can also be trans-apical, trans-atrial, and direct aortic delivery of a prosthetic replacement valve to a target location in the heart. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The devices and methods described herein provide a valve replacement device that can be recaptured in a delivery device after being only partially deployed to reposition and/or remove the device. The device also has the flexibility to adapt and conform to the variably-shaped native mitral valve anatomy while mechanically isolating the prosthetic valve from the anchoring portion of the device. Several embodiments of the device effectively absorb the distorting forces applied by the native anatomy. The device has the structural strength and integrity necessary to withstand the dynamic conditions of the heart over time, thus permanently anchoring a replacement valve. The devices and methods further deliver such a device in a less-invasive manner, providing a patient with a new, permanent replacement valve but also with a lower-risk procedure and a faster recovery.
Access to the Mitral Valve To better understand the structure and operation of valve replacement devices in accordance with the present technology, it is helpful to first understand approaches for implanting the devices. The mitral valve or other type of atrioventricular valve (such as the tricuspid valve TV) can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
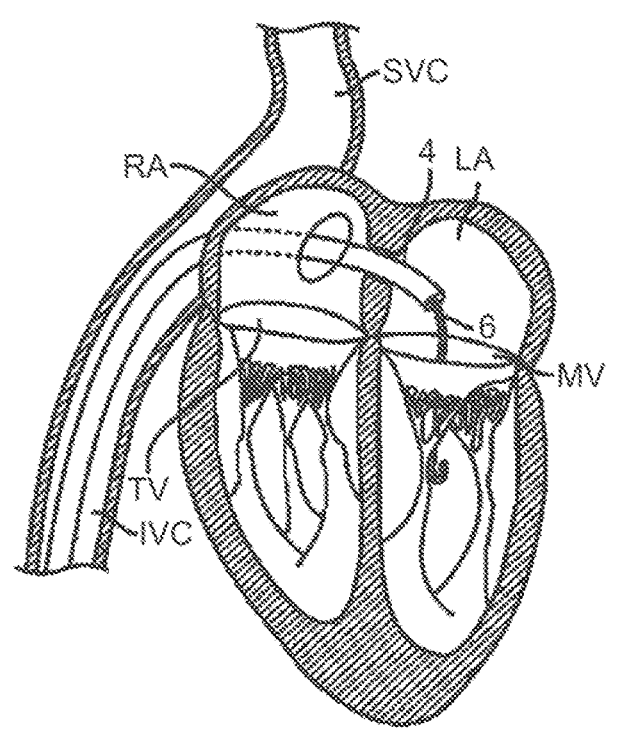
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendineae (CT) or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
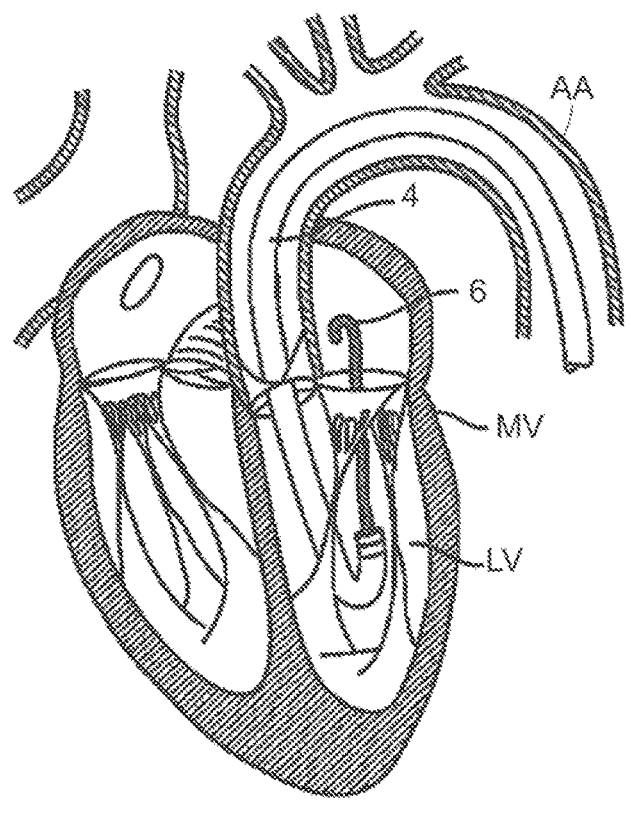
FIGS. 3 and 4 are schematic, cross-sectional illustrations of the heart showing retrograde approaches to the native mitral valve through the aortic valve and arterial vasculature in accordance with various embodiments of the present technology.
Figure 4:
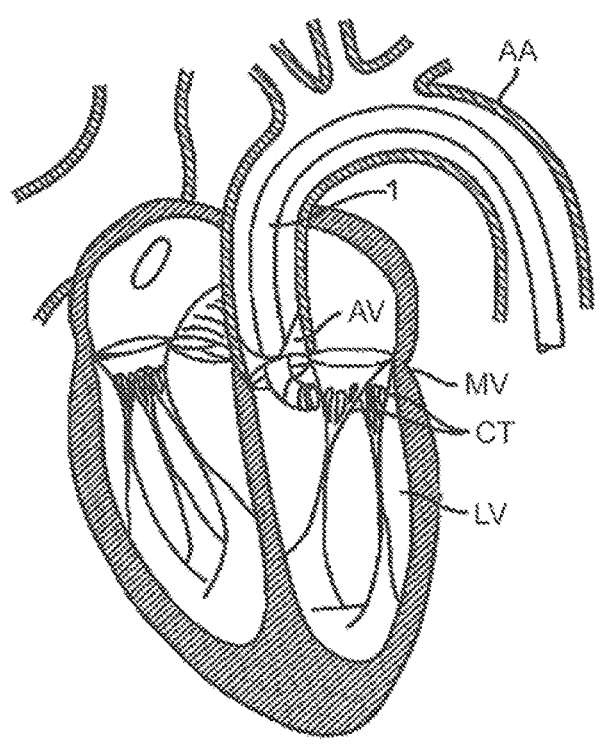

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
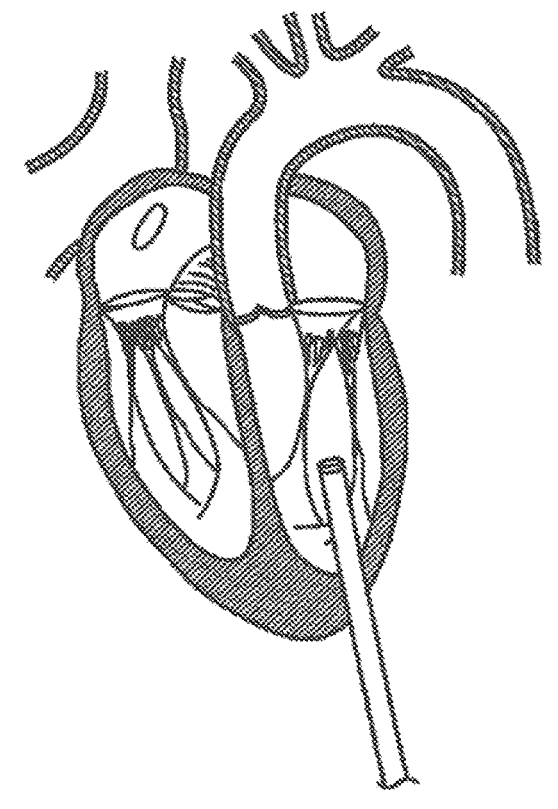
FIG. 5 is a schematic, cross-sectional illustration of the heart showing an approach to the native mitral valve using a trans-apical puncture in accordance with various embodiments of the present technology.

FIG. 5 shows a trans-apical approach via a trans-apical puncture. In this approach, access to the heart is via a thoracic incision, which can be a conventional open thoracotomy or sternotomy, or a smaller intercostal or sub-xyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Prosthetic Heart Valve Devices and Methods

Embodiments of the present technology can treat one or more of the valves of the heart, and in particular several embodiments advantageously treat the mitral valve. The prosthetic valve devices of the present technology can also be suitable for replacement of other valves (e.g., a bicuspid or tricuspid valve) in the heart of the patient. Examples of prosthetic heart valve devices, system components and associated methods in accordance with embodiments of the present technology are described in this section with reference to FIGS. 6A-19. Specific elements, substructures, advantages, uses, and/or other features of the embodiments described with reference to FIGS. 6A-19 can be suitably interchanged, substituted or otherwise configured with one another. Furthermore, suitable elements of the embodiments described with reference to FIGS. 6A-19 can be used as stand-alone and/or self-contained devices.

Figure 6A:
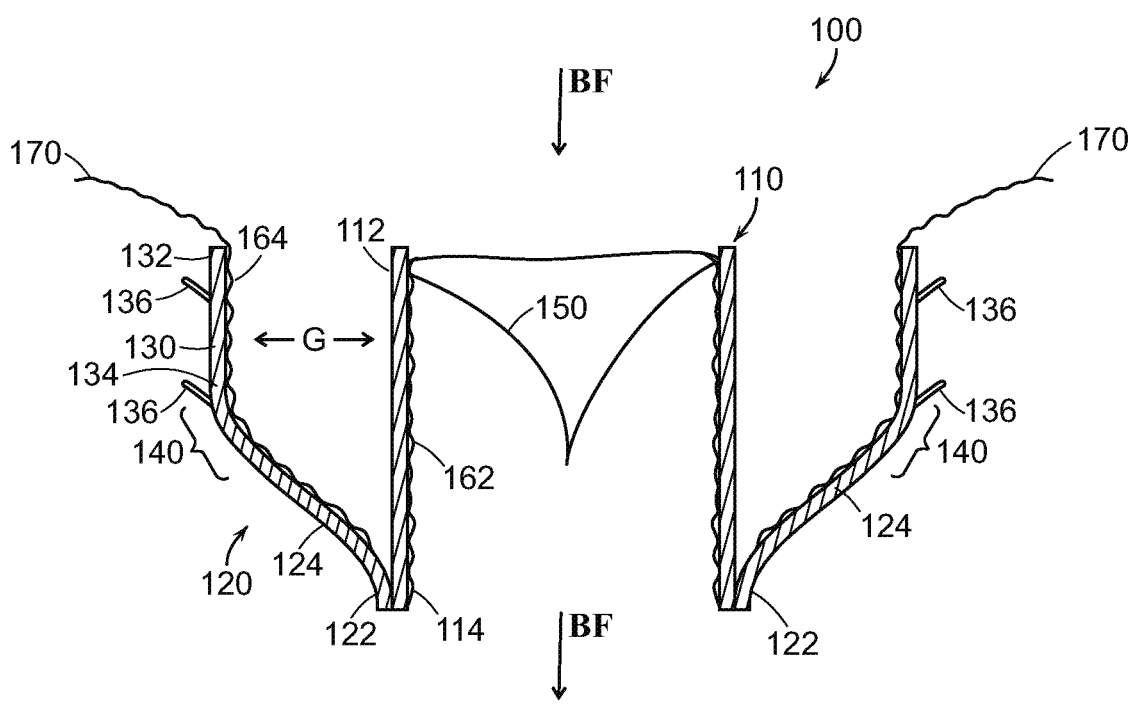
FIG. 6A is a cross-sectional side view and FIG. 6B is a top view schematically illustrating a prosthetic heart valve device in accordance with an embodiment of the present technology.
Figure 6B:
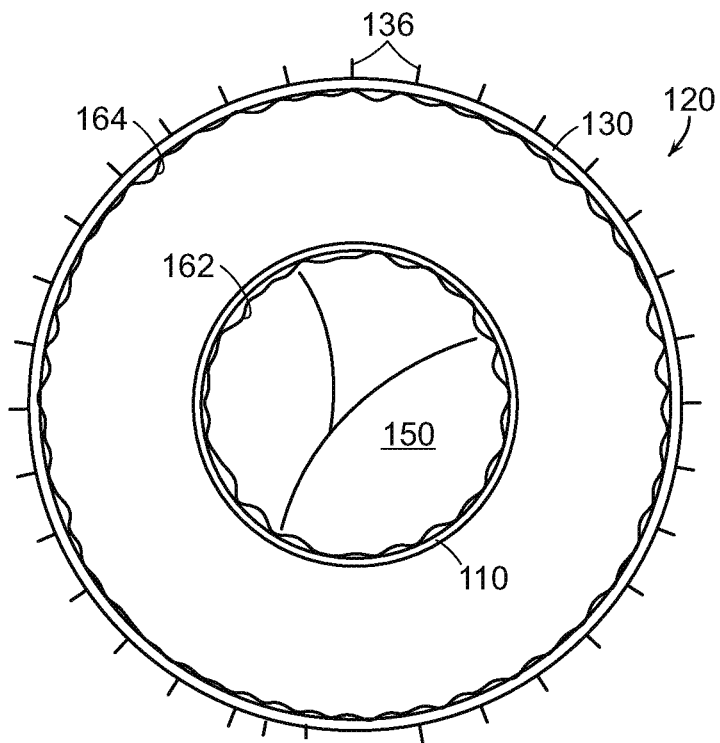

FIG. 6A is a side cross-sectional view and FIG. 6B is a top plan view of a prosthetic heart valve device ("device") 100 in accordance with an embodiment of the present technology. The device 100 includes a valve support 110, an anchoring member 120 attached to the valve support 110, and a prosthetic valve assembly 150 within the valve support 110. Referring to FIG. 6A, the valve support 110 has an inflow region 112 and an outflow region 114. The prosthetic valve assembly 150 is arranged within the valve support 110 to allow blood to flow from the inflow region 112 through the outflow region 114 (arrows BF), but prevent blood from flowing in a direction from the outflow region 114 through the inflow region 112.

In the embodiment shown in FIG. 6A, the anchoring member 120 includes a base 122 attached to the outflow region 114 of the valve support 110 and a plurality of arms 124 projecting laterally outward from the base 122. The anchoring member 120 also includes a fixation structure 130 extending from the arms 124. The fixation structure 130 can include a first portion 132 and a second portion 134. The first portion 132 of the fixation structure 130, for example, can be an upstream region of the fixation structure 130 that, in a deployed configuration as shown in FIG. 6A, is spaced laterally outward apart from the inflow region 112 of the valve support 110 by a gap G. The second portion 134 of the fixation structure 130 can be a downstream-most portion of the fixation structure 130. The fixation structure 130 can be a cylindrical ring (e.g., straight cylinder or conical), and the outer surface of the fixation structure 130 can define an annular engagement surface configured to press outwardly against the native annulus. The fixation structure 130 can further include a plurality of fixation elements 136 that project radially outward and are inclined toward an upstream direction. The fixation elements 136, for example, can be barbs, hooks, or other elements that are inclined only in the upstream direction (e.g., a direction extending away from the downstream portion of the device 100).

Referring still to FIG. 6A, the anchoring member 120 has a smooth bend 140 between the arms 124 and the fixation structure 130. For example, the second portion 134 of the fixation structure 130 extends from the arms 124 at the smooth bend 140. The arms 124 and the fixation structure 130 can be formed integrally from a continuous strut or support element such that the smooth bend 140 is a bent portion of the continuous strut. In other embodiments, the smooth bend 140 can be a separate component with respect to either the arms 124 or the fixation structure 130. For example, the smooth bend 140 can be attached to the arms 124 and/or the fixation structure 130 using a weld, adhesive or other technique that forms a smooth connection. The smooth bend 140 is configured such that the device 100 can be recaptured in a capsule or other container after the device 100 has been at least partially deployed.

The device 100 can further include a first sealing member 162 on the valve support 110 and a second sealing member 164 on the anchoring member 120. The first and second sealing members 162, 164 can be made from a flexible material, such as Dacron® or another type of polymeric material. The first sealing member 162 can cover the interior and/or exterior surfaces of the valve support 110. In the embodiment illustrated in FIG. 6A, the first sealing member 162 is attached to the interior surface of the valve support 110, and the prosthetic valve assembly 150 is attached to the first sealing member 162 and commissure portions of the valve support 110. The second sealing member 164 is attached to the inner surface of the anchoring member 120. As a result, the outer annular engagement surface of the fixation structure 130 is not covered by the second sealing member 164 so that the outer annular engagement surface of the fixation structure 130 directly contacts the tissue of the native annulus.

The device 100 can further include an extension member 170. The extension member 170 can be an extension of the second sealing member 164, or it can be a separate component attached to the second sealing member 164 and/or the first portion 132 of the fixation structure 130. The extension member 170 can be a flexible member that, in a deployed state as shown in FIG. 6A, flexes relative to the first portion 132 of the fixation structure 130. In operation, the extension member 170 provides tactile feedback or a visual indicator (e.g., on echocardiographic or fluoroscopic imaging systems) to guide the device 100 during implantation such that the device is located at a desired elevation and centered relative to the native annulus. As described below, the extension member 170 can include a support member, such as a metal wire or other structure, that can be visualized during implantation. For example, the support member can be a radiopaque wire.

Figures 7A, 7B:
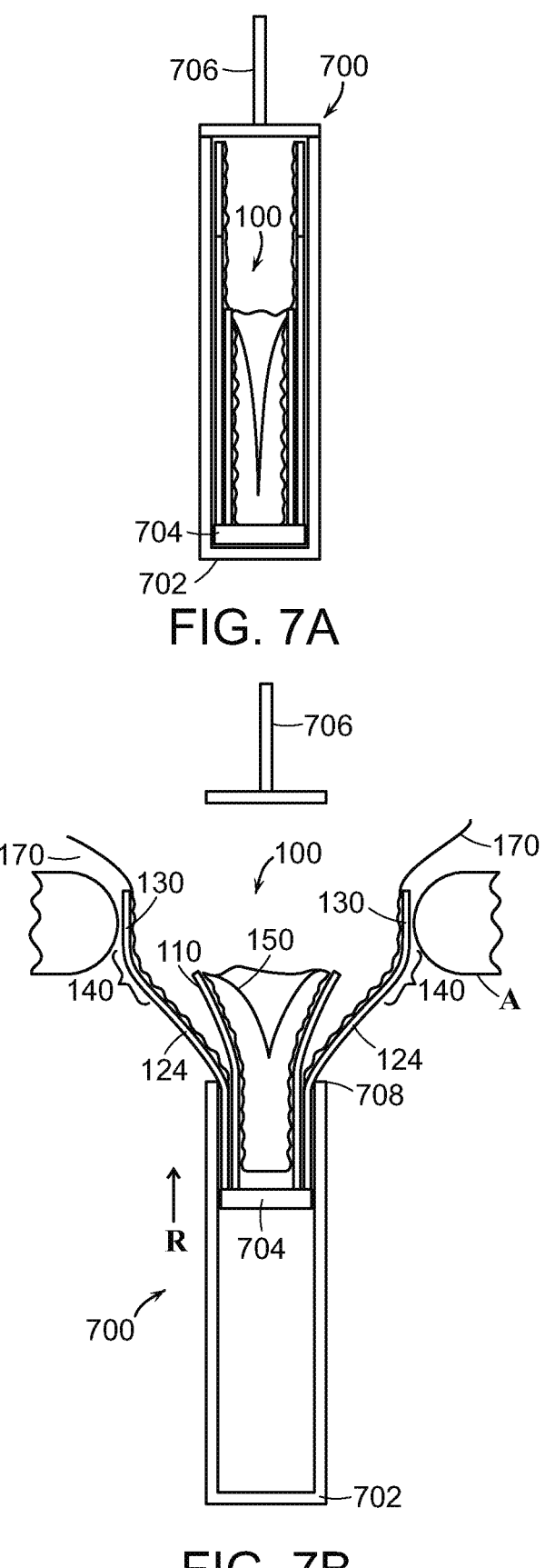
FIGS. 7A and 7B are cross-sectional side views schematically illustrating aspects of delivering a prosthetic heart valve device in accordance with an embodiment of the present technology.

FIGS. 7A and 7B are cross-sectional views illustrating an example of the operation of the smooth bend 140 between the arms 124 and the fixation structure 130 in the recapturing the device 100 after partial deployment. FIG. 7A schematically shows the device 100 loaded into a capsule 700 of a delivery system in a delivery state, and FIG. 7B schematically shows the device 100 in a partially deployed state. Referring to FIG. 7A, the capsule 700 has a housing 702, a support 704, and a top 706. In the delivery state shown in FIG. 7A, the device 100 is in a low-profile configuration suitable for delivery through a catheter or cannula to a target implant site at a native heart valve.

Referring to FIG. 7B, the housing 702 of the capsule 700 has been moved distally such that the extension member 170, fixation structure 130 and a portion of the arms 124 have been released from the housing 702 in a partially deployed state. This is useful for locating the fixation structure 130 at the proper elevation relative to the native valve annulus A such that the fixation structure 130 expands radially outward and contacts the inner surface of the native annulus A. However, the device 100 may need to be repositioned and/or removed from the patient after being partially deployed. To do this, the housing 702 is retracted (arrow R) back toward the fixation structure 130. As the housing 702 slides along the arms 124, the smooth bend 140 between the arms 124 and the fixation structure 130 allows the edge 708 of the housing 702 to slide over the smooth bend 140 and thereby recapture the fixation structure 130 and the extension member 170 within the housing 702. The device 100 can then be removed from the patient or repositioned for redeployment at a better location relative to the native annulus A. Further aspects of prosthetic heart valve devices in accordance with the present technology and their interaction with corresponding delivery devices are described below with reference to FIGS. 8-19.

FIG. 8 is a top isometric view of an example of the device 100. In this embodiment, the valve support 110 defines a first frame (e.g., an inner frame) and fixation structure 130 of the anchoring member 120 defines a second frame (e.g., an outer frame) that each include a plurality of structural elements. The fixation structure 130, more specifically, includes structural elements 137 arranged in diamond-shaped cells 138 that together form at least a substantially cylindrical ring when freely and fully expanded as shown in FIG. 8. The structural elements 137 can be struts or other structural features formed from metal, polymers, or other suitable materials that can self-expand or be expanded by a balloon or other type of mechanical expander.

Several embodiments of the fixation structure 130 can be a generally cylindrical fixation ring having an outwardly facing engagement surface. For example, in the embodiment shown in FIG. 8, the outer surfaces of the structural elements 137 define an annular engagement surface configured to press outwardly against the native annulus in the deployed state. In a fully expanded state without any restrictions, the fixation structure 130 is at least substantially parallel to the valve support 110. However, the fixation structure 130 can flex inwardly (arrow I) in the deployed state when it presses radially outwardly against the inner surface of the native annulus of a heart valve.

The embodiment of the device 100 shown in FIG. 8 includes the first sealing member 162 lining the interior surface of the valve support 110, and the second sealing member 164 along the inner surface of the fixation structure 130. The extension member 170 has a flexible web 172 (e.g., a fabric) and a support member 174 (e.g., metal or polymeric strands) attached to the flexible web 172. The flexible web 172 can extend from the second sealing member 164 without a metal-to-metal connection between the fixation structure 130 and the support member 174. For example, the extension member 170 can be a continuation of the material of the second sealing member 164. Several embodiments of the extension member 170 are thus a floppy structure that can readily flex with respect to the fixation structure 130. The support member 174 can have a variety of configurations and be made from a variety of materials, such as a double-serpentine structure made from Nitinol.

Figure 10:
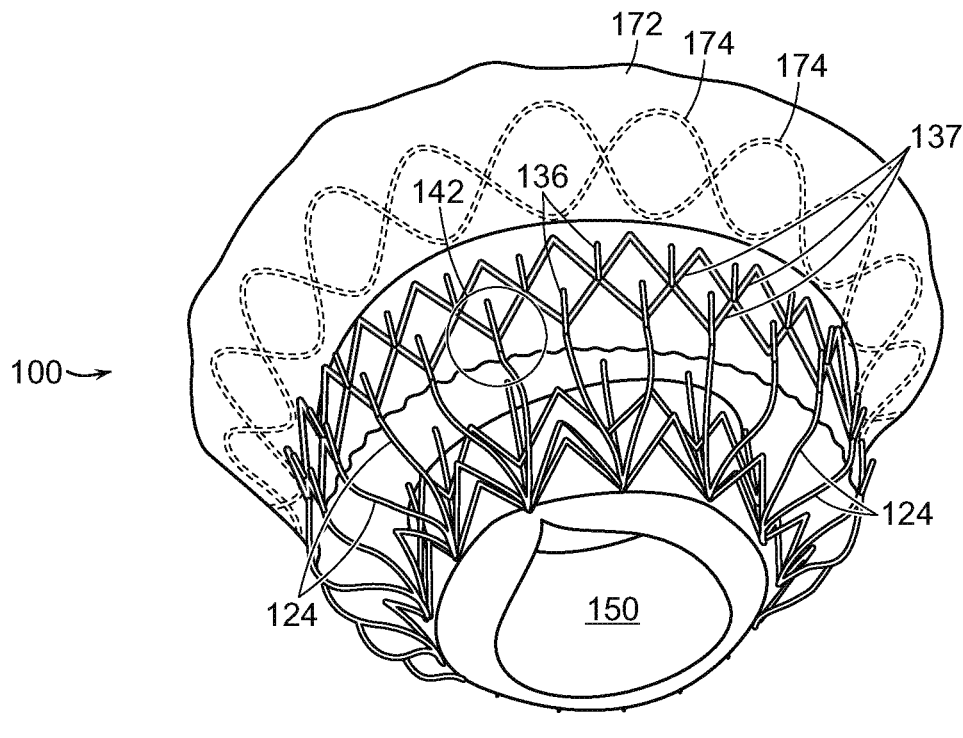
FIG. 10 is a bottom isometric view of the prosthetic heart valve device of FIG. 9A.

FIG. 9A is a side view, FIG. 9B is a detailed view of a portion of FIG. 9A, and FIG. 10 is a bottom isometric view of the device 100 shown in FIG. 8. Referring to FIG. 9A, the arms 124 extend radially outward from the base portion 122 at an angle α selected to position the fixation structure 130 radially outward from the valve support 110 (FIG. 8) by a desired distance in a deployed state. The angle α is also selected to allow the edge 708 of the housing 702 (FIG. 7B) to slide from the base portion 122 toward the fixation structure 130 during recapturing. In many embodiments, the angle α is 15°-75°, or more specifically 15°-60°, or still more specifically 30°-45°. The arms 124 and the structural elements 137 of the fixation structure 130 can be formed from the same struts (i.e., formed integrally with each other) such that the smooth bend 140 is a continuous, smooth transition from the arms 124 to the structural elements 137. This is expected to enable the edge 708 of the housing 702 to more readily slide over the smooth bend 140 in a manner that allows the fixation structure 130 to be recaptured in the housing 702 of the capsule 700 (FIG. 7B). Additionally, by integrally forming the arms 124 and the structural elements 137 with each other, it reduces the potential of breaking the device 100 at a junction between the arms 124 and the structural elements 137 compared to a configuration in which the arms 124 and structural elements 137 are separate components and welded or otherwise fastened to each other. FIGS. 9A and 9B also show that the device 100 can further include chevron-support struts at the outflow region that extend between the arms 124 at the base 122 of the anchoring member 120. The chevron-supports at the base 122 do not necessarily have a "smooth bend," such as the smooth bend 140 at the transition from the arms 124 to the downstream-most portion of the fixation structure 130. As such, so long as the chevron-supports and other elements of the device 100 project toward the inflow region to allow recapture, certain portions of the device 100, and the anchoring member 120 in particular, need not have such a smooth bend.

Referring to FIGS. 9B and 10, the arms 124 are arranged in V-shaped arm units 125 that each have a pair of arms 124 extending from a bifurcation 127 at the base portion 122. In this embodiment, the individual arms 124 in each V-shaped arm unit 125 are separated from each other along their entire length from where they are connected to the base portion 122 through the smooth bend 140 (FIG. 9A) to the structural elements 137 of the fixation structure 130. The individual arms 124 are thus able to readily flex as the edge 708 of the housing 702 (FIG. 7B) slides along the arms 124 during recapturing. This is expected to reduce the likelihood that the edge 708 of the housing 702 will catch on the arms 124 and prevent the device 100 from being recaptured in the housing 702.

In one embodiment, the arms 124 have a first length from the base 122 to the smooth bend 140, and the structural elements 137 of the fixation structure 130 at each side of a cell 138 (FIG. 8) have a second length. The second length of the structural elements 137 along each side of a cell 138 is less than the first length of the arms 124. The fixation structure 130 is accordingly less flexible than the arms 124. As a result, the fixation structure 130 is able to press outwardly against the native annulus with sufficient force to secure the device 100 to the native annulus, while the arms 124 are sufficiently flexible to fold inwardly when the device is recaptured in a delivery device.

In the embodiment illustrated in FIGS. 8-10, the arms 124 and the structural elements 137 are configured such that each arm 124 and the two structural elements 137 extending from each arm 124 formed a Y-shaped portion 142 (FIG. 10) of the anchoring member 120. Additionally, the right-hand structural element 137 of each Y-shaped portion 142 is coupled directly to a left-hand structural element 137 of an immediately adjacent Y-shaped portion 142. The Y-shaped portions 142 and the smooth bends 140 are expected to further enhance the ability to slide the housing 702 along the arms 124 and the fixation structure 130 during recapturing.

Figure 11:
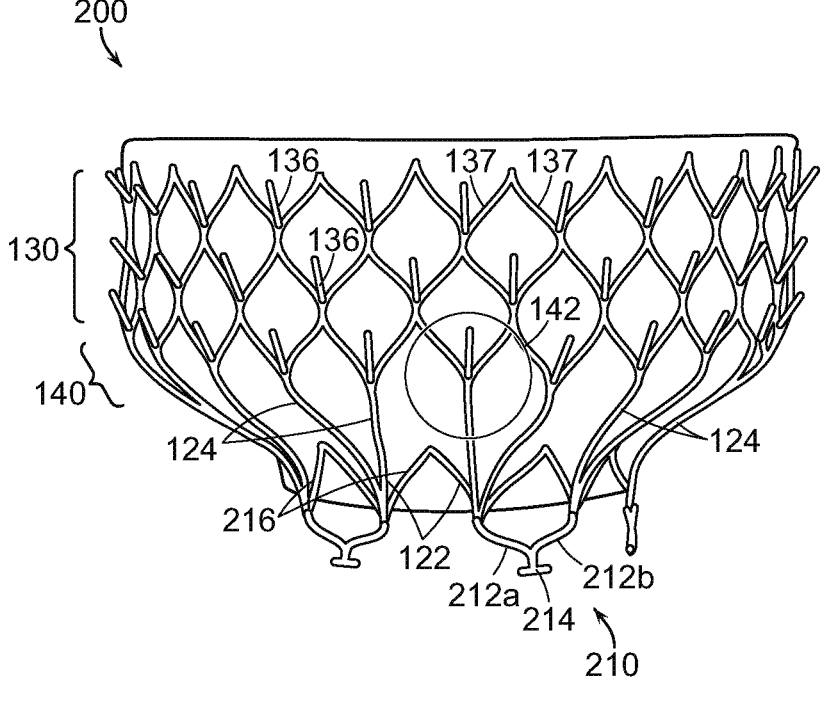
FIG. 11 is a side view and FIG. 12A is a bottom isometric view of a prosthetic heart valve device in accordance with an embodiment of the present technology.
Figure 12A:
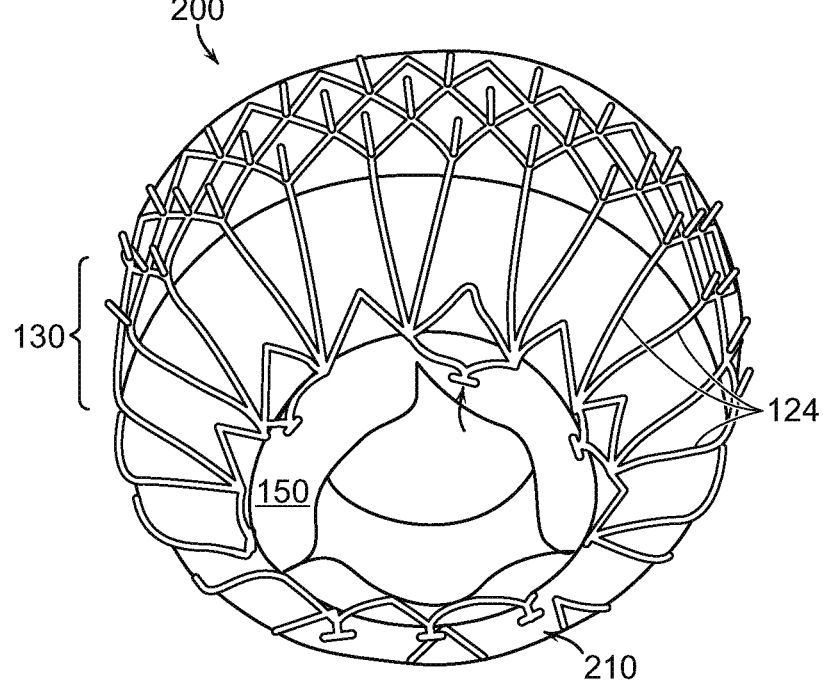

FIG. 11 is a side view and FIG. 12A is a bottom isometric view of a prosthetic heart valve device ("device") 200 in accordance with another embodiment of the present technology. The device 200 is shown without the extension member 170 (FIGS. 8-10), but the device 200 can further include the extension member 170 described above. The base 122 of the device 200 shown in FIG. 12A further includes only a single row of chevron-supports 216 as opposed to the dual-rows of chevron-supports at the base 122 of the device 100 shown in FIG. 10. The device 200 further includes extended connectors 210 projecting from the base 122 of the anchoring member 120. Alternatively, the extended connectors 210 can extend from the valve support 110 (FIGS. 6A-10) in addition to or in lieu of extending from the base 122 of the anchoring member 120. The extended connectors 210 can include a first strut 212*a* attached to one portion of the base 122 and a second strut 212*b* attached to another portion of the base 122. The first and second struts 212*a*-*b* are configured to form a V-shaped structure in which they extend toward each other in a downstream direction and are connected to each other at the bottom of the V-shaped structure. The V-shaped structure of the first and second struts 212*a*-*b* causes the extension connector 210 to elongate when the device 200 is in a low-profile configuration within the capsule 700 (FIG. 7A) during delivery or partial deployment. When the device 200 is fully released from the capsule 700 (FIG. 7A) the extension connectors 210 foreshorten to avoid interfering with blood flow along the left ventricular outflow tract.

The extended connectors 210 further include an attachment element 214 configured to releasably engage a delivery device. The attachment element 214 can be a T-bar or other element that prevents the device 200 from being released from the capsule 700 (FIG. 7A) of a delivery device until desired. For example, a T-bar type attachment element 214 can prevent the device 200 from moving axially during deployment or partial deployment until the housing 702 (FIG. 7A) moves distally beyond the attachment elements 214 such that the outflow region of the valve support 110 and the base 122 of the anchoring member 120 can fully expand upon full deployment.

Figures 12B, 12C:
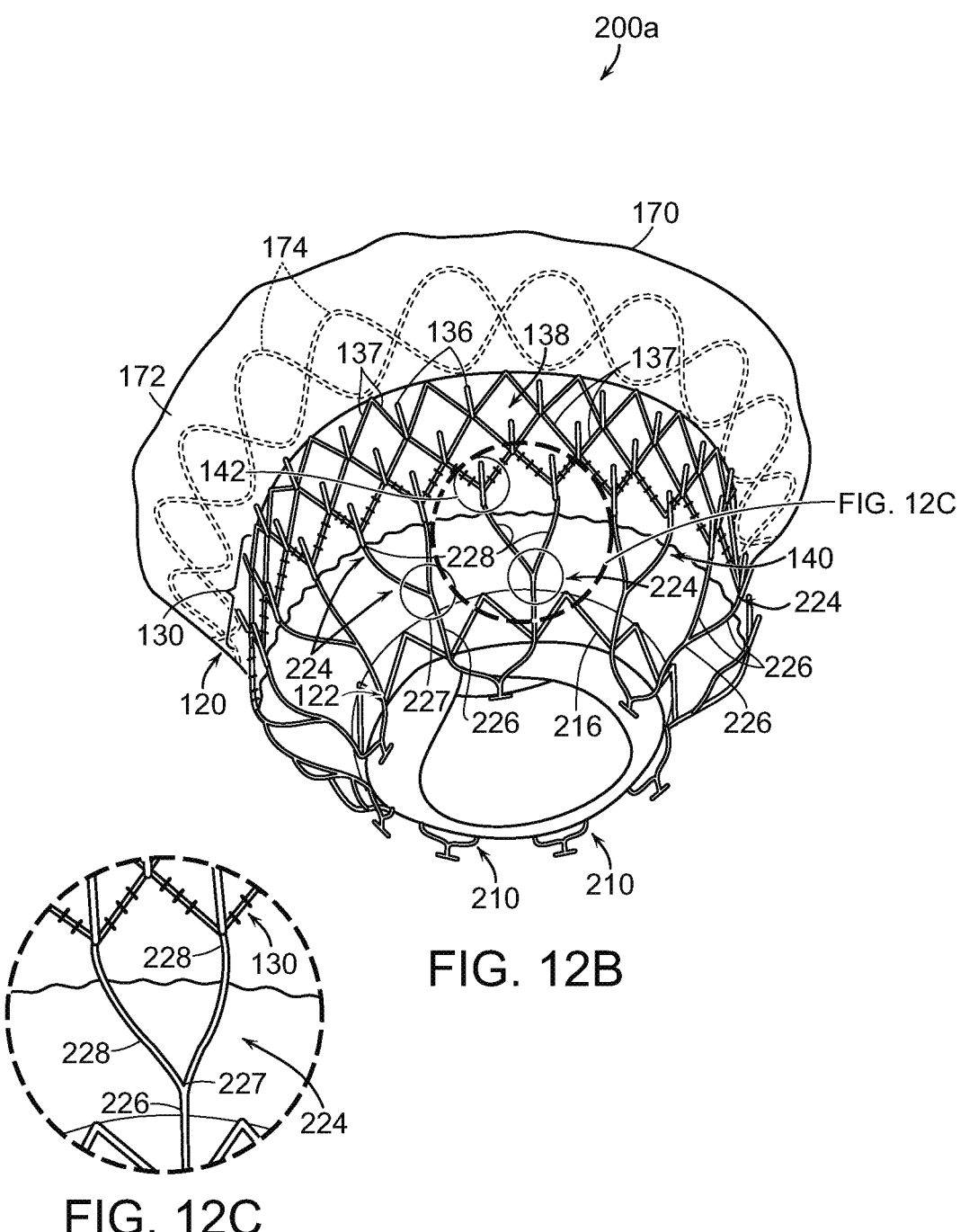
FIG. 12B is an isometric view of a prosthetic heart valve device in accordance with another embodiment of the present technology.
FIG. 12C is a detailed view of a portion of the heart valve device shown in FIG. 12B.

FIG. 12B is an isometric view of a prosthetic heart valve device 200*a* ("device 200*a*") in accordance with another embodiment of the present technology, and FIG. 12C is a detailed view of an arm unit of the device 200*a*. The device 200*a* is substantially similar to the device 200 shown in FIG. 12A, but the device 200*a* includes a plurality of Y-shaped arm units 224 instead of V-shaped arm units. Referring to FIG. 12C, the arm units 224 have a trunk 226 and two arms 228 extending from the trunk 226 at a bifurcation 227. The trunk 226 of each Y-shaped arm unit 224 extends from a single row of chevron-supports 216 at the base 122 of the anchoring member 120, and the trunks 226 have a length such that the bifurcations 227 are located a distance apart from the base 122. The arms 228 of the Y-shaped arm units 224 can be slightly shorter than the arms 124 of the V-shaped arm units 125 described above with respect to FIG. 9B, but the overall lengths of the Y-shaped and V-shaped arm units 224 and 125 can be about the same. The Y-shaped arm units

Figure 13:
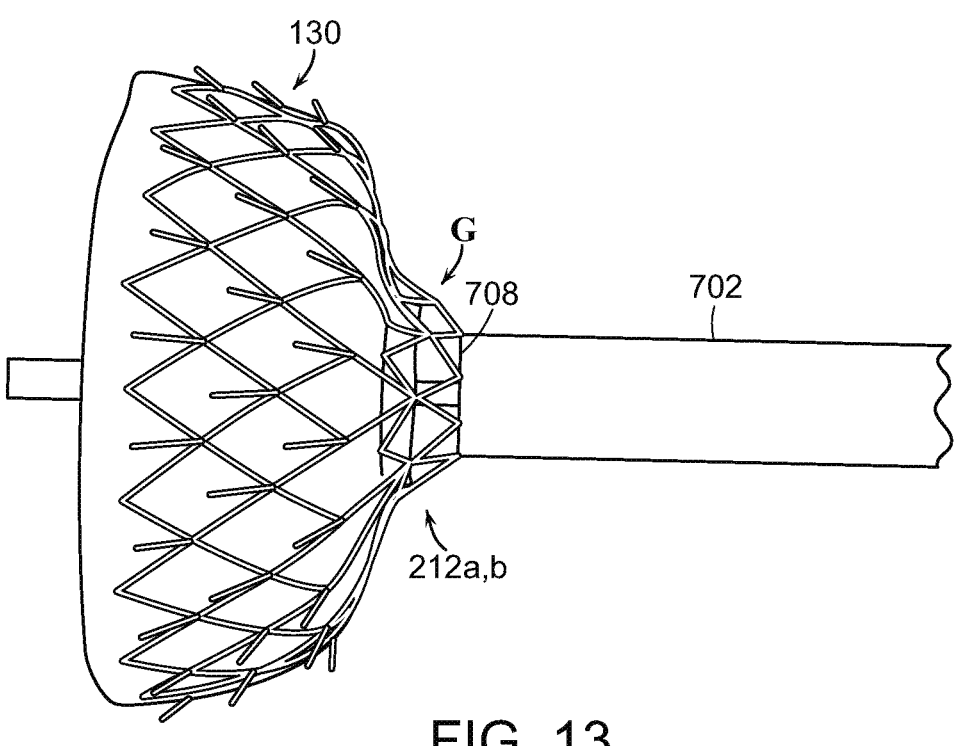
FIG. 13 is a side view and FIG. 14 is a bottom isometric view of the prosthetic heart valve device of FIGS. 11 and 12 at a partially deployed state with respect to a delivery device.
Figure 14:
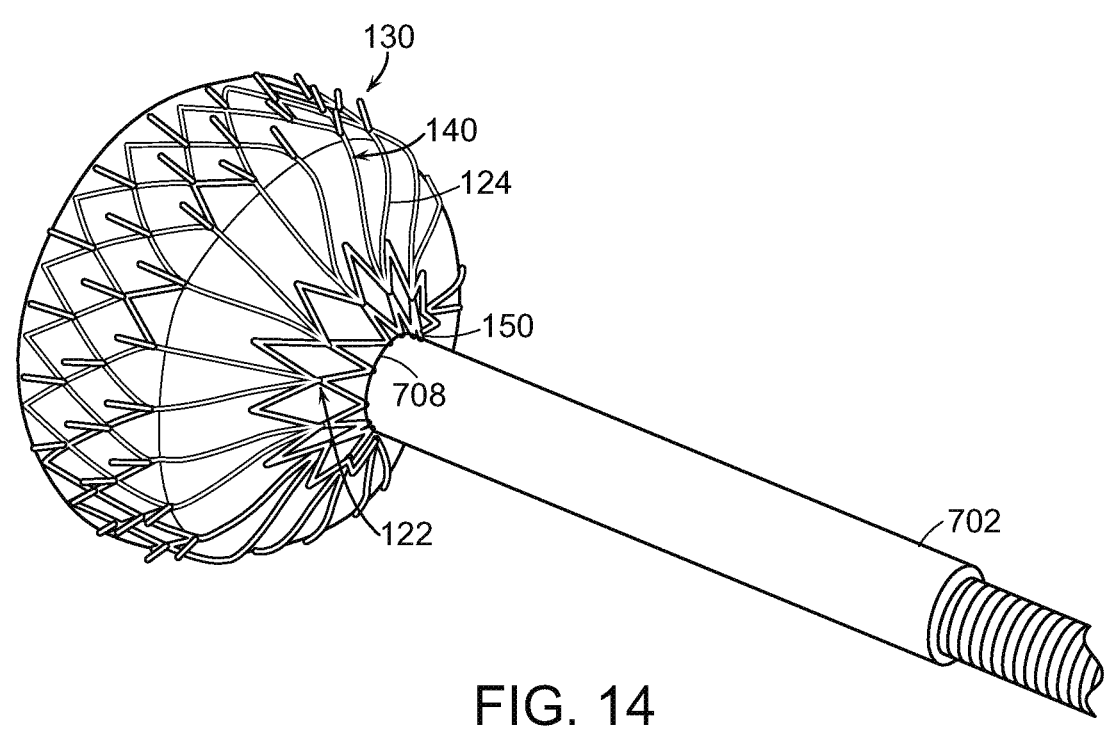

224 reduce the amount of metal in the region of the chevron-supports 216 compared to the V-shaped arm units 125, which reduces the material at the base 122 of the anchoring member 120 so that the device 200*a* can be crimped to a smaller diameter for delivery. Moreover, the Y-shaped arm units 224 are also sufficiently flexible so that the device 200*a* can be resheathed in a capsule of a delivery device. FIG. 13 is a side view and FIG. 14 is a bottom isometric view of the device 200 in a partially deployed state in which the device 200 is still capable of being recaptured in the housing 702 of the delivery device 700. Referring to FIG. 13, the device 200 is partially deployed with the fixation structure 130 substantially expanded but the attachment elements 214 (FIG. 11) still retained within the capsule 700. This is useful for determining the accuracy of the position of the device 200 and allowing blood to flow through the functioning replacement valve during implantation while retaining the ability to recapture the device 200 in case it needs to be repositioned or removed from the patient. In this state of partial deployment, the elongated first and second struts 212*a*-*b* of the extended connectors 210 space the base 122 of the anchoring member 120 and the outflow region of the valve support 110 (FIG. 6A) apart from the edge 708 of the capsule 702 by a gap G.

Referring to FIG. 14, the gap G enables blood to flow through the prosthetic valve assembly 150 while the device 200 is only partially deployed. As a result, the device 200 can be partially deployed to determine (a) whether the device 200 is positioned correctly with respect to the native heart valve anatomy and (b) whether proper blood flow passes through the prosthetic valve assembly 150 while the device 200 is still retained by the delivery system 700. As such, the device 200 can be recaptured if it is not in the desired location and/or if the prosthetic valve is not functioning properly. This additional functionality is expected to significantly enhance the ability to properly position the device 200 and assess, in vivo, whether the device 200 will operate as intended, while retaining the ability to reposition the device 200 for redeployment or remove the device 200 from the patient.

Figure 15:
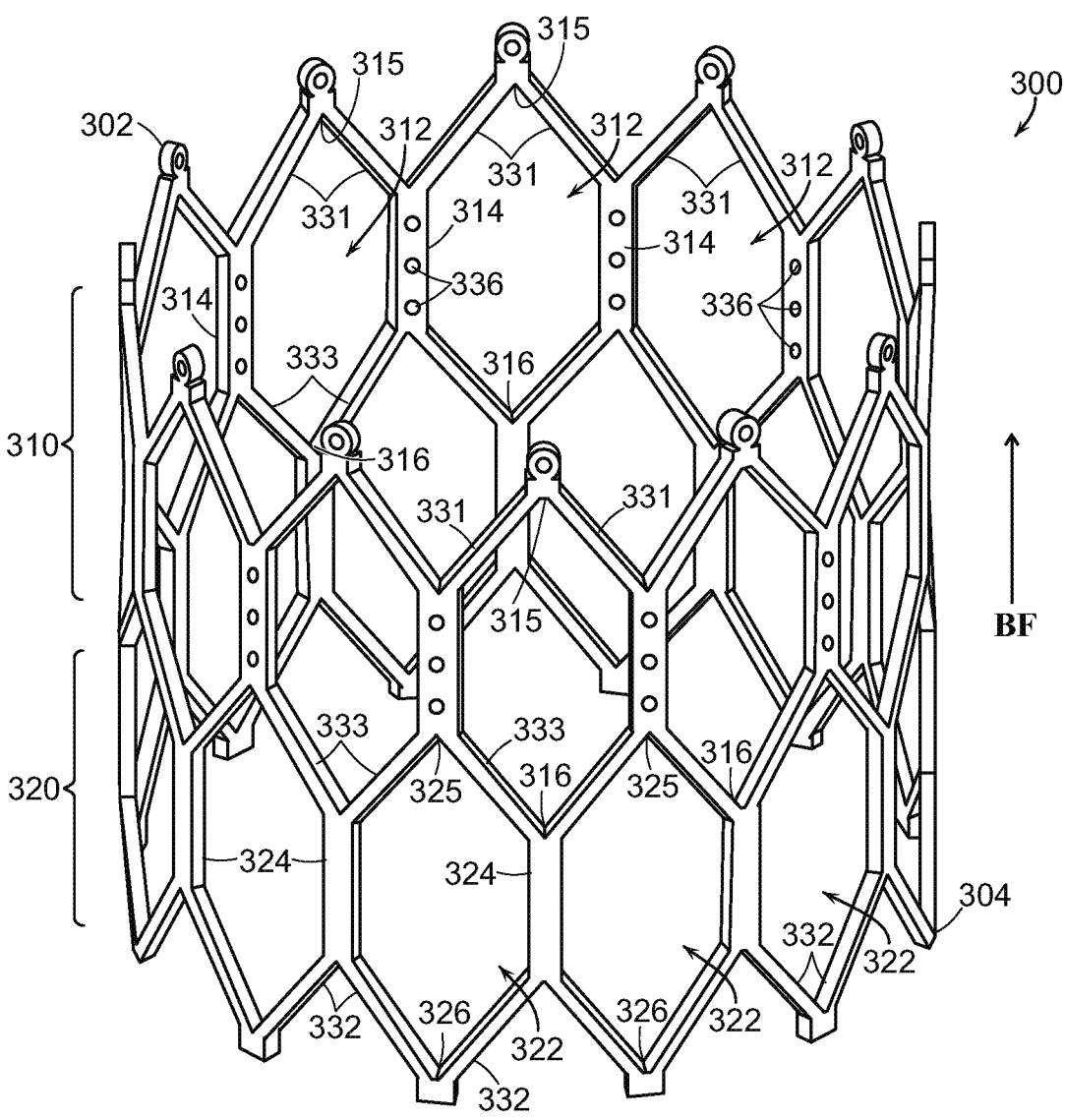
FIG. 15 is a bottom isometric view of a valve support for use with prosthetic heart valve devices in accordance with the present technology.

FIG. 15 is a bottom isometric view of a valve support 300 in accordance with an embodiment of the present technology. The valve support 300 can be an embodiment of the valve support 110 described above with respect to FIGS. 6A-14. The valve support 300 has an outflow region 302, an inflow region 304, a first row 310 of first hexagonal cells 312 at the outflow region 302, and a second row 320 of second hexagonal cells 322 at the inflow region 304. The valve support shown in FIG. 15 is inverted compared to the valve support 100 shown in FIGS. 6A-14 for purposes of illustration such that the blood flows through the valve support 300 in the direction of arrow BF. In mitral valve applications, the valve support 300 would be positioned within the anchoring member 120 (FIG. 6A) such that the inflow region 304 would correspond to orientation of the inflow region 112 in FIG. 6A and the outflow region 302 would correspond to the orientation of the outflow region 114 in FIG. 6A.

Each of the first hexagonal cells 312 includes a pair of first longitudinal supports 314, a downstream apex 315, and an upstream apex 316. Each of the second hexagonal cells 322 can include a pair of second longitudinal supports 324, a downstream apex 325, and an upstream apex 326. The first and second rows 310 and 320 of the first and second hexagonal cells 312 and 322 are directly adjacent to each other. In the illustrated embodiment, the first longitudinal supports 314 extend directly from the downstream apexes 325 of the second hexagonal cells 322, and the second longitudinal supports 324 extend directly from the upstream apexes 316 of the first hexagonal cells 312. As a result, the first hexagonal cells 312 are offset circumferentially from the second hexagonal cells 322 around the circumference of the valve support 300 by half of the cell width.

In the embodiment illustrated in FIG. 15, the valve support 300 includes a plurality of first struts 331 at the outflow region 302, a plurality of second struts 332 at the inflow region 304, and a plurality of third struts 333. Each of the first struts 331 extends from a downstream end of the first longitudinal supports 314, and pairs of the first struts 331 are connected together to form first downstream V-struts defining the downstream apexes 315 of the first hexagonal cells 312. In a related sense, each of the second struts 332 extends from an upstream end of the second longitudinal supports 324, and pairs of the second struts 332 are connected together to form second upstream V-struts defining the upstream apexes 326 of the second hexagonal cells 322. Each of the third struts 333 has a downstream end connected to an upstream end of the first longitudinal supports 314, and each of the third struts 333 has an upstream end connected to a downstream end of one of the second longitudinal supports 324. The downstream ends of the third struts 333 accordingly define a second downstream V-strut arrangement that forms the downstream apexes 325 of the second hexagonal cells 322, and the upstream ends of the third struts 333 define a first upstream V-strut arrangement that forms the upstream apexes 316 of the first hexagonal cells 312. The third struts 333, therefore, define both the first upstream V-struts of the first hexagonal cells 312 and the second downstream V-struts of the second hexagonal cells 322.

The first longitudinal supports 314 can include a plurality of holes 336 through which sutures can pass to attach a prosthetic valve assembly and/or a sealing member. In the embodiment illustrated in FIG. 15, only the first longitudinal supports 314 have holes 336. However, in other embodiments the second longitudinal supports 324 can also include holes either in addition to or in lieu of the holes 336 in the first longitudinal supports 314.

Figure 17:
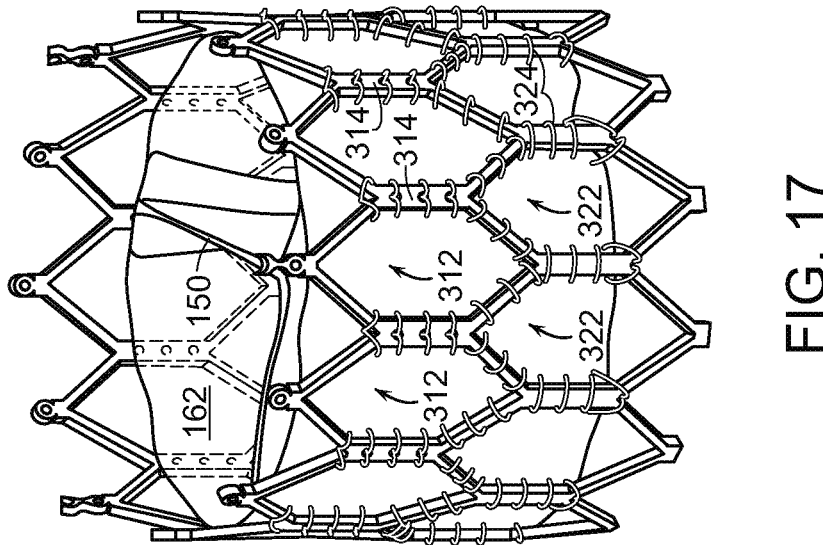
FIGS. 16 and 17 are side and bottom isometric views, respectively, of a prosthetic heart valve attached to the valve support of FIG. 15.
Figure 16:
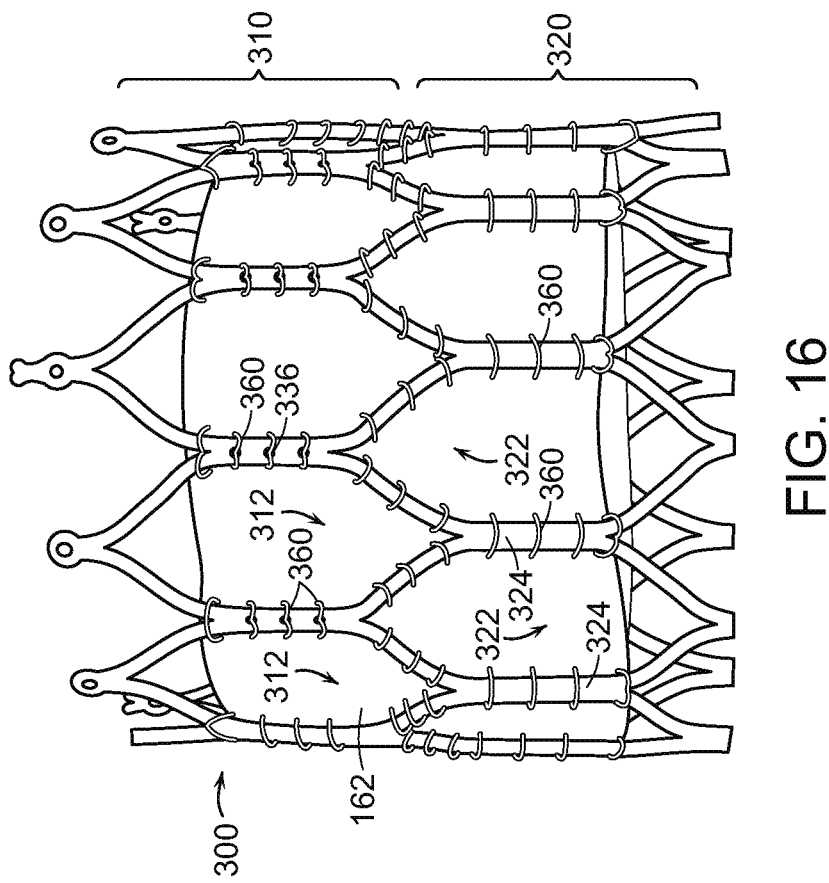

FIG. 16 is a side view and FIG. 17 is a bottom isometric view of the valve support 300 with a first sealing member 162 attached to the valve support 300 and a prosthetic valve 150 within the valve support 300. The first sealing member 162 can be attached to the valve support 300 by a plurality of sutures 360 coupled to the first longitudinal supports 314 and the second longitudinal supports 324. At least some of the sutures 360 coupled to the first longitudinal supports 314 pass through the holes 336 to further secure the first sealing member 162 to the valve support 300. Sutures 360 can also pass through the holes 336 if holes 336 are included in addition to or in lieu of the holes 336 of the first longitudinal supports 314.

Referring to FIG. 17, the prosthetic valve 150 can be attached to the first sealing member 162 and/or the first longitudinal supports 314 of the valve support 300. For example, the commissure portions of the prosthetic valve 150 can be aligned with the first longitudinal supports 314, and the sutures 360 can pass through both the commissure portions of the prosthetic valve 150 and the first sealing member 162 where the commissure portions of the prosthetic valve 150 are aligned with a first longitudinal support 314. The inflow portion of the prosthetic valve 150 can be sewn to the first sealing member 162.

The valve support 300 illustrated in FIGS. 15-17 is expected to be well suited for use with the device 100 and 200 and described above with reference to FIGS. 8-10 and 11-14, respectively. More specifically, the first struts 331 cooperate with the base of the anchoring member 122. The first struts 331, for example, elongate when the valve support 300 is not fully expanded compared to when the valve support is fully expanded. In addition to the elongation of the struts, the position of the prosthetic valve 150 within the valve support 300 allows the outflow portion of the prosthetic valve 150 to be spaced further apart from the capsule 700 in a partially deployed state so that the prosthetic valve 150 can at least partially function in the partially deployed state. Alternatively, if attached to the device 200, the extended connectors 210 (FIGS. 11-14) of the device 200 serve to further separate the outflow portion of the prosthetic valve 150 from the capsule 700 (FIGS. 13-14) when the device 200 is in a partially deployed state, allowing for partial function of the prosthetic valve 150. Upon full deployment, the first struts 331 foreshorten. Therefore, the valve support 300 is expected to enhance the ability to assess whether the prosthetic valve 150 is fully operational in a partially deployed state. This additional functionality is expected to significantly enhance the ability to assess, in vivo, whether the device 100 and 200 will operate as intended, while retaining the ability to reposition the device 100 and 200 for redeployment or remove the device 100 and 200 from the patient.

Figure 18:
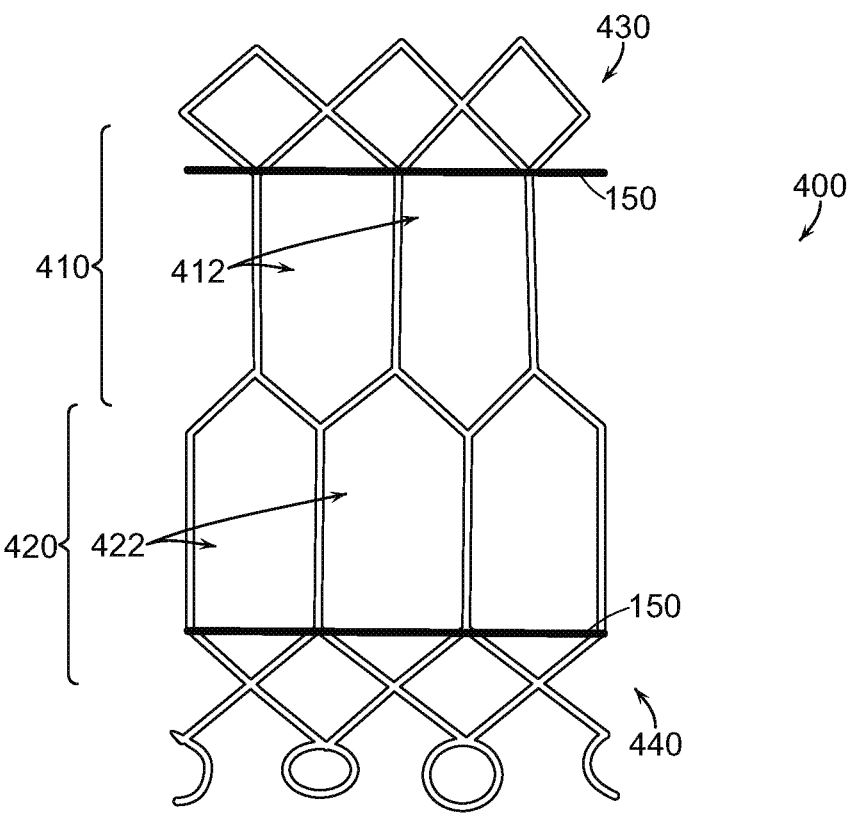
FIGS. 18 and 19 are side views schematically showing valve supports in accordance with additional embodiments of the present technology.
Figure 19:
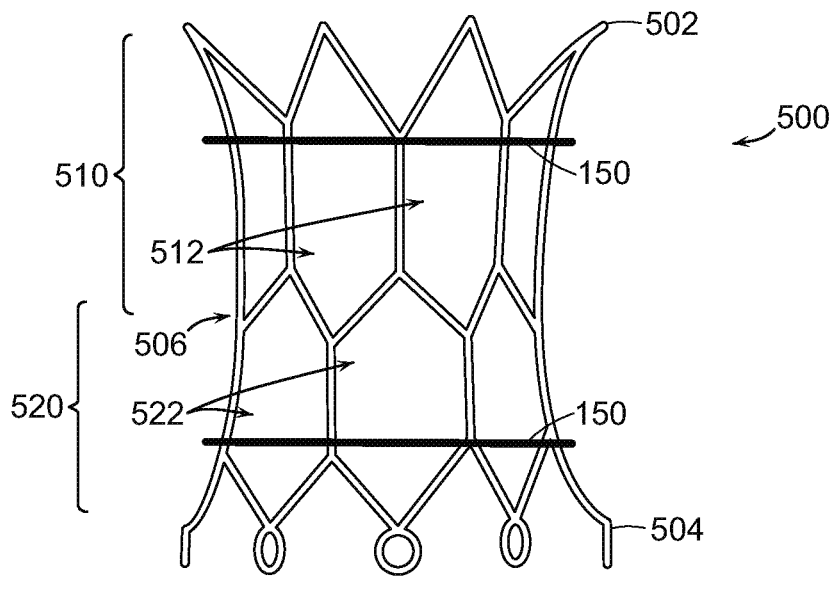

FIGS. 18 and 19 are schematic side views of valve supports 400 and 500, respectively, in accordance with embodiments of the present technology. The valve support 400 includes a first row 410 of first of hexagonal cells 412 and a second row 420 of second hexagonal cells 422. The valve 400 can further include a first row 430 of diamond-shaped cells extending from the first hexagonal cells 412 and a second row 440 of diamond-shaped cells extending from the second hexagonal cells 422. The additional diamond-shaped cells elongate in the low-profile state, and thus they can further space the prosthetic valve 150 (shown schematically) apart from the capsule of the delivery device, enhancing the ability to assess, in vivo, whether the device will operate as intended while retaining the ability to reposition or remove the device from the patient. Referring to FIG. 19, the valve support 500 includes a first row 510 of first hexagonal cells 512 at an outflow region 502 and a second row 520 of second hexagonal cells 522 at an inflow region 504. The valve support 500 is shaped such that an intermediate region 506 has a smaller cross-sectional area than that of the outflow region 502 and/or the inflow region 504. As such, the first row 510 of first hexagonal cells 512 flares outwardly in the downstream direction and the second row 520 of second hexagonal cells 522 flares outwardly in the upstream direction. The flared outflow and inflow regions 502 and 504 are expected to improve blood flow through the valve support 500. Additionally, the flared outflow and inflow regions 502 and 504 reduce the length of the valve support compared to a straight cylindrical design, which reduces the amount that the valve support 500 extends into the left ventricle.

Figure 20:
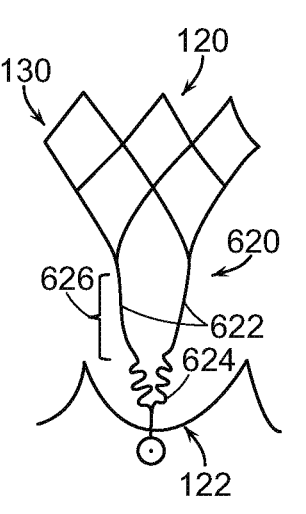
FIG. 20 is a schematic view of an arm unit of an anchoring member for use with prosthetic heart valve devices in accordance with the present technology.

FIG. 20 is a schematic view showing a portion of an anchoring member 120 in accordance with an embodiment of the present technology. In this embodiment, the anchoring member 120 includes the fixation structure 130 and V-shaped arm units 620 (only a single arm unit shown). Each V-shaped arm unit 620 includes a pair of arms 622 extending from the base 122 to the fixation structure 130 (only a portion shown), and each arm 622 includes a first portion 624 having a first flexibility and a second portion 626 with a second flexibility less than the first flexibility. The first portion 624 of the arms 622 are selectively flexible at the base 122 of the anchoring member 120, while the second portion 626 of the arms 622 have sufficient stiffness to push the fixation structure 130 radially outwardly for engaging the native annulus. In the illustrated embodiment, the first portion 624 of the arms 622 are a serpentine member (e.g., an according connector), and the second portion 626 of the arms 622 are straighter than the first portion 624. For example the second portion 626 of the arms 622 can curve radially outward along an arc (e.g. a single arc) as opposed to the serpentine or the zig-zag configuration of the first portion 624.

Figure 21:
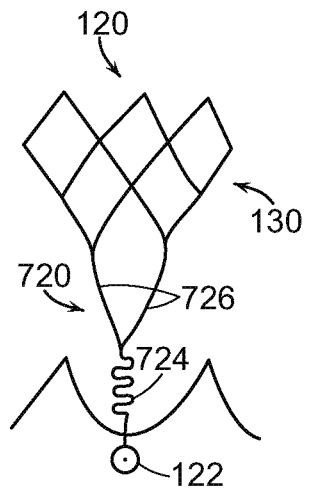
FIG. 21 is a schematic view of an arm unit of an anchoring member for use with prosthetic heart valve devices in accordance with the present technology.

FIG. 21 is a schematic view showing a portion of another anchoring member 120 in accordance with an embodiment of the present technology including Y-shaped arm units 720 (only a single arm unit 720 shown). Each Y-shaped arm unit 720 has a trunk 724 and arms 726 extending from the trunk 724. The trunk 724 has a first flexibility, and the arms 726 have a second flexibility less than the first flexibility. The trunk 724, for example, is a strut having a serpentine configuration (e.g., an accordion connector), and the arms 726 can be curved struts extending radially outward from the trunk 724 in an expanded configuration.

Figure 22:
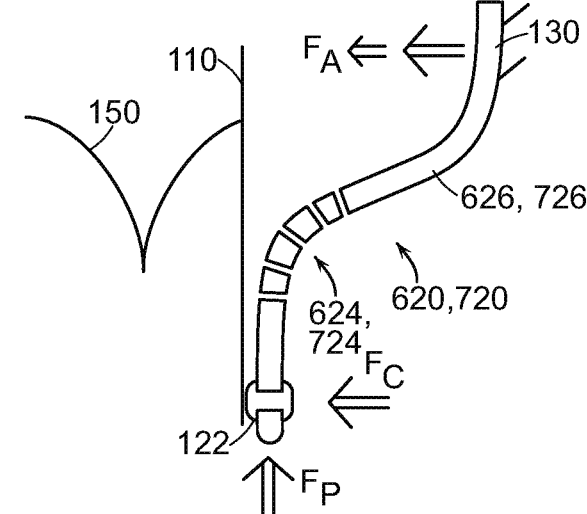
FIG. 22 is a schematic view of a portion of the arm units of FIGS. 20 and 21 in accordance with the present technology.

FIG. 22 schematically illustrates the operation of the arm units 620 and 720 shown in FIGS. 20 and 21. In operation, the native annulus (not shown) exerts a compressive annulus force $F_A$ against the fixation structure 130 while the systolic pressure creates a force FP. The additional flexibility of the first portion 624 or the trunk 724 allows the arm units 620 and 720 to preferentially flex near the outflow end of the valve support 110 to allow the fixation structure 130 to be deformed by the native annulus while mitigating the commissure forces Fc exerted against the valve support 110 at the base 122. Notably, the second portion 626 of the arms 622 and the arms 726 are sufficiently stiff to provide the desired radially outward force against the native annulus for securing the prosthetic heart valve device at the native heart valve.

Figure 23:
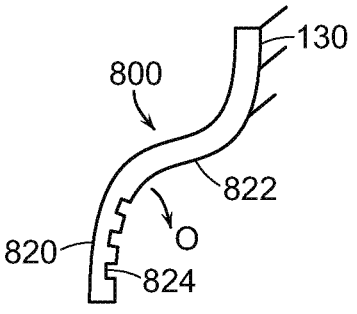
FIG. 23 is a schematic view of an arm unit of an anchoring member for use with prosthetic heart valve devices in accordance with the present technology.

FIG. 23 illustrates an arm 800 supporting a fixation structure 130 in accordance with another embodiment of the present technology. The arm 800 can include a first portion 820 configured to be coupled to the outflow region of a valve support and a second portion 822 extending from the first portion 820 to the fixation structure 130. The first portion 820 of the arm 800 can correspond to the first portion 624 of the arms 622 of the V-shaped arm unit 620 or the trunk 724 of the Y-shaped arm unit 720. The first portion 820 of the arm 800 can further include a plurality of outward recesses 824 (e.g., notches) that enable the first portion 822 preferentially flex outward (arrow O). The arm 800 is expected to perform substantially similarly to the arms 622 and the Y-shaped arm unit 720 described above with reference to FIGS. 20-22.

Figure 24A:
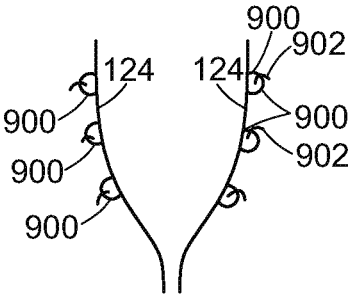
FIGS. 24A and 24B are schematic views showing arms having difference configurations of eyelets for coupling a sealing member to an anchoring member in accordance with the present technology.
Figure 24B:
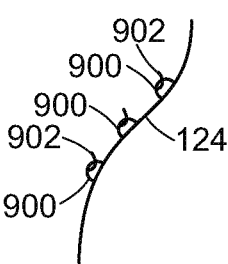

FIGS. 24A and 24B are schematic views showing arms 124 having difference configurations of eyelets 900 for coupling the second sealing member 164 (FIGS. 6A and 6B) to the anchoring member 120. Referring to FIG. 24A, the eyelets 900 are on the outside of the arms 124. Referring to FIG. 24B, the eyelets are on the inside of the arms 124. In both embodiments, sutures 902 pass through the eyelets to attach the second sealing member 164 to the inside of the anchoring member 120. The embodiment shown in FIG. 24B is particularly well-suited for resheathing the prosthetic heart valve devices because the eyelets are shape-set to extend inwardly to eliminate or otherwise limit protrusions relative to the outer surface of the arms 124 that could inhibit the capsule from sliding over the arms 124 during resheathing.

EXAMPLES

Several aspects of the present technology described above are embodied in the following examples.

1. A prosthetic heart valve device for treating a native valve of a human heart having a native annulus and native leaflets, comprising:

a valve support having an inflow region and an outflow region;

a prosthetic valve assembly within the valve support; and an anchoring member having a base attached to the outflow region of the valve support, a plurality of arms projecting laterally outward from the base and inclined in an upstream direction in a deployed state, and a fixation structure extending upstream from the arms, the fixation structure having a plurality of struts that define an annular engagement surface configured to press outwardly against the native annulus and a plurality of fixation elements projecting from the struts, wherein a downstream-most portion of the fixation structure extends from the arms at a smooth bend and fixation elements at the downstream-most portion of the fixation structure extend in an upstream direction.

2. The prosthetic heart valve device of example 1 wherein the arms are spaced apart from each other throughout their length.

3. The prosthetic heart valve device of any of examples 1-2 wherein the struts of the fixation structure are arranged in cells having sides, and the arms have a first length and each side of the cells has a second length less than the first length.

4. The prosthetic heart valve device of any of examples 1-3 wherein each arm and the struts of the fixation structure extending from each arm form a Y-shaped portion of the anchoring member, and a right-hand strut of each Y-shaped portion is coupled directly to a left-hand strut of an immediately adjacent Y-shaped portion.

5. The prosthetic heart valve device of any of examples 1-4, further comprising connector extensions projecting from a downstream end of the valve support and/or the base, and wherein each connector extension has first and second struts forming a V-shaped structure extending downstream from the valve support and/or the base, and a connector projecting downstream from the V-shaped structure, wherein the connector is configured to be releasably held by a delivery device.

6. The prosthetic heart valve device of any of examples 1-5 wherein all of the fixation elements projecting from the fixation structure extend in an upstream direction.

7. The prosthetic heart valve device of any of examples 1-6 wherein the valve support comprises:

a first row of first hexagonal cells at the outflow region of the valve support, and the first hexagonal cells having first longitudinal supports;

a second row of second hexagonal cells at the inflow region of the valve support, the second hexagonal cells having second longitudinal supports, wherein the first and second hexagonal cells are directly adjacent to each other such that the first longitudinal supports extend directly from downstream apexes of the second hexagonal cells and the second longitudinal supports extend directly from upstream apexes of the first hexagonal cells; and wherein the prosthetic valve assembly is attached to at least one of the first longitudinal supports and/or at least one of the second longitudinal supports.

8. The prosthetic heart valve device of example 7 wherein the valve support further comprises a first row of diamond-shaped cells at a downstream end of the first row of hexagonal cells and a second row of diamond-shaped cells at an upstream end of the second row of hexagonal cells.

9. The prosthetic heart valve device of example 7 wherein the first row of hexagonal cells flares outward in the downstream direction and the second row of hexagonal cells flares outward in the upstream direction.

10. The prosthetic heart valve device of example 7, further comprising connector extensions projecting from a downstream end of the valve support and/or the base, and wherein each connector extension has first and second struts forming a V-shaped structure extending downstream from the valve support and/or the base, and a connector projecting downstream from the V-shaped structure, wherein the connector is configured to be releasably held by a delivery device.

11. The prosthetic heart valve device of any of examples 1-10 wherein the valve support comprises:

a first row of first hexagonal cells at the outflow region of the valve support, wherein the first hexagonal cells have first longitudinal supports, first upstream V-struts extending upstream from the first longitudinal supports, and first downstream V-struts extending downstream from the first longitudinal supports;

a second row of second hexagonal cells at the inflow region of the valve support, wherein the second hexagonal cells have second longitudinal supports, second upstream V-struts extending upstream from the second longitudinal supports, and second downstream V-struts extending downstream from the second longitudinal supports; and wherein the first upstream V-struts of the first hexagonal cells and the second downstream inverted V-struts of the second hexagonal cells are the same struts.

12. A prosthetic heart valve device for treating a native valve of a human heart having a native annulus and native leaflets, comprising:

an annular inner support frame having an inflow region and an outflow region;

a prosthetic valve assembly within the inner support frame; and an anchoring member having a base attached to the outflow region of the inner support frame, a plurality of arms projecting laterally outward from the base at an angle inclined in an upstream direction, and an outer fixation frame extending upstream from the arms, the outer fixation frame having a plurality of struts that define an annular engagement surface spaced radially outward from the inflow region of the inner support frame in the deployed state, wherein the arms and the struts are configured to be partially deployed from a capsule and then at least substantially recaptured within the capsule by moving at least one of the capsule and/or the device relative to the other such the arms and struts slide into the capsule.

13. The prosthetic heart valve device of example 12 wherein the arms are spaced apart from each other throughout their length.

14. The prosthetic heart valve device of any of examples 12-13 wherein the struts of the outer fixation frame are arranged in cells having sides, and the arms have a first length and each side of the cells has a second length less than the first length.

15. The prosthetic heart valve device of any of examples 12-14 wherein each arm and the struts of the outer fixation frame extending from each arm form a Y-shaped portion of the anchoring member, and a right-hand strut of each Y-shaped portion is coupled directly to a left-hand strut of an immediately adjacent Y-shaped portion.

16. The prosthetic heart valve device of any of examples 12-15, further comprising connector extensions projecting from a downstream end of the inner annular support frame and/or the base, and wherein each connector extension has first and second struts forming a V-shaped structure extending downstream from the inner annular support frame and/or the base, and a connector projecting downstream from the V-shaped structure, wherein the connector is configured to be releasably held by a delivery device.

17. The prosthetic heart valve device of any of examples 12-16, further comprising fixation elements projecting from the outer fixation frame, and wherein all of the fixation elements project from the outer fixation frame extend in an upstream direction.

18. The prosthetic heart valve device of any of examples 12-17 wherein the inner annular support frame comprises:

a first row of first hexagonal cells at the outflow region of the inner annular support frame, and the first hexagonal cells having first longitudinal supports;

a second row of second hexagonal cells at the inflow region of the inner annular support frame, the second hexagonal cells having second longitudinal supports, wherein the first and second hexagonal cells are directly adjacent to each other such that the first longitudinal supports extend directly from downstream apexes of the second hexagonal cells and the second longitudinal supports extend directly from upstream apexes of the first hexagonal cells; and wherein the prosthetic valve assembly is attached to at least one of the first longitudinal supports and/or at least one of the second longitudinal supports.

19. The prosthetic heart valve device of example 18 wherein the inner annular support frame further comprises a first row of diamond-shaped cells at a downstream end of the first row of hexagonal cells and a second row of diamond-shaped cells at an upstream end of the second row of hexagonal cells.

20. The prosthetic heart valve device of example 18 wherein the first row of hexagonal cells flares outward in the downstream direction and the second row of hexagonal cells flares outward in the upstream direction.

21. The prosthetic heart valve device of example 18, further comprising connector extensions projecting from a downstream end of the inner annular support frame and/or the base, and wherein each connector extension has first and second struts forming a V-shaped structure extending downstream from the inner annular support frame and/or the base, and a connector projecting downstream from the V-shaped structure, wherein the connector is configured to be releasably held by a delivery device.

22. The prosthetic heart valve device of any of examples 1-21 wherein the arms are arranged in pairs defining V-shaped arm units.

23. The prosthetic heart valve device of example 22 wherein the V-shaped arm units have a pair of arm, and each arm has a first portion having a first flexibility and a second portion having a second flexibility less than the first flexibility.

24. The prosthetic heart valve device of example 23 wherein the first portion has a serpentine configuration.

25. the prosthetic heart valve device of example 23 wherein the first portion has outwardly open notches.

26. The prosthetic heart valve device of any of examples 1, 3-12 and 14-21 wherein the arms are arranged in Y-shaped arm units having a trunk and a pair of arms extending from the trunk.

27. The prosthetic heart valve device of examples 26 wherein the trunk has a first flexibility and the arms have a second flexibility less than the first flexibility.

28. The prosthetic heart valve device of example 27 wherein the trunk has a serpentine configuration.

29. The prosthetic heart valve device of example 27 wherein the trunk has a plurality of outwardly open notches.

30. A method of deploying a prosthetic heart valve device for treating a native heart valve, comprising:

partially deploying a prosthetic heart valve device from a capsule of a delivery device such that an inflow region of a valve support and an inflow region of a fixation structure are expanded radially outward relative to the capsule with the inflow region of the fixation structure being spaced radially outward of the valve support, wherein an outflow region of the valve support and/or the fixation structure remains within the capsule, and wherein a gap exists between a downstream end of a prosthetic valve within the valve support and a distal terminus of the capsule such that fluid can flow through the valve while the outflow region is within the capsule; and recapturing the prosthetic heart valve device within the capsule.

31. The method of example 30 wherein the native heart valve is a native mitral valve.

32. The method of example 30 wherein the native heart valve is a native aortic valve.

33. A valve support for a prosthetic heart valve, comprising:

a first row of first hexagonal cells at an outflow region of the valve support, wherein the first hexagonal cells have first longitudinal supports, first and second upstream struts extending upstream from the first longitudinal supports, and first and second downstream struts extending downstream from the first longitudinal supports;

a second row of second hexagonal cells at an inflow region of the valve support, wherein the second hexagonal cells have second longitudinal supports, first and second upstream struts extending upstream from the second longitudinal supports, and first and second downstream struts extending downstream from the second longitudinal supports; and wherein the first and second upstream struts of the first hexagonal cells and the first and second downstream struts of the second hexagonal cells are the same struts.

34. The valve support of example 33 wherein the first and second longitudinal supports have a first width and the first and second upstream struts and the first and second downstream struts have a second width less than the first width.

35. The valve support of any of examples 33-34 wherein:

the first and second hexagonal cells are directly adjacent to each other such that the first longitudinal supports extend directly from downstream apexes of the second hexagonal cells and the second longitudinal supports extend directly from upstream apexes of the first hexagonal cells; and wherein the prosthetic valve assembly is attached to at least one of the first longitudinal supports and/or at least one of the second longitudinal supports.

36. The prosthetic heart valve device of any of examples 33-35 wherein the valve support further comprises a first row of diamond-shaped cells at a downstream end of the first row of hexagonal cells and a second row of diamond-shaped cells at an upstream end of the second row of hexagonal cells.

37. The prosthetic heart valve device of any of examples 33-36 wherein the first row of hexagonal cells flares outward in the downstream direction and the second row of hexagonal cells flares outward in the upstream direction.

38. The prosthetic heart valve device of any of examples 33-37, further comprising connector extensions projecting from a downstream end of the first hexagonal cells, and wherein each connector extension has first and second struts forming a V-shaped structure extending downstream from the first hexagonal cells, and a connector projecting downstream from the V-shaped structure, wherein the connector is configured to be releasably held by a delivery device.

From the foregoing, it will be appreciated that specific embodiments of the invention have been described herein for purposes of illustration, but that various modifications may be made without deviating from the scope of the invention. For example, several individual components can be interchange with each other in the different embodiments. Accordingly, the invention is not limited except as by the appended claims.

I claim:

1. A prosthetic heart valve device comprising:

a valve support having a first region and a second region;

a prosthetic valve assembly disposed within the valve support; and an anchoring member comprising:

a base attached to the first region of the valve support;

a plurality of arm units projecting laterally outward from the base and inclined in a direction away from the first region in a deployed state, each arm unit including a first portion coupled to the base and a second portion; and a fixation structure extending from the second portion of the arm units, the fixation structure having a plurality of struts that define an annular engagement surface configured to press outwardly against a native annulus of a native heart valve;

wherein the first portion of each arm unit has a first flexibility and the second portion of each arm unit as a second flexibility, wherein the first flexibility is greater than the second flexibility.

2. The prosthetic heart valve device of claim 1, wherein each arm unit is a V-shaped arm unit having two arms coupled to the base, the two arms extending laterally away from each other from the base to the fixation structure, each of the two arms having the first portion with the first flexibility and the second portion with the second flexibility.

3. The prosthetic heart valve device of claim 2, wherein the first portion of each arm is serpentine.

4. The prosthetic heart valve device of claim 1, wherein each arm unit is a Y-shaped arm unit having a trunk coupled to the base and two arms extending from the trunk to the fixation structure.

5. The prosthetic heart valve device of claim 4, wherein the trunk is the first portion of the arm unit and the two arms are the second portion of the arm unit.

6. The prosthetic heart valve device of claim 5, wherein only the trunk is serpentine.

7. The prosthetic heart valve device of claim 1, wherein the first region is an outflow region of the valve support and the second region is an inflow region of the valve support.

8. The prosthetic heart valve device of claim 1, further comprising a sealing member coupled to an inner surface of the anchoring member.

9. The prosthetic heart valve device of claim 8, wherein the arm units include eyelets, wherein sutures pass through the eyelets to attach the sealing member to the inner surface of the anchoring member.

10. The prosthetic heart valve device of claim 9, wherein eyelets are coupled to the inner surface of the arm units.

11. The prosthetic heart valve device of claim 9, wherein eyelets are coupled to an outer surface of the arm units.

12. A prosthetic heart valve device comprising:

an inner stent having a first region and a second region;

a prosthetic valve assembly disposed within the inner stent; and an outer stent comprising:

a base attached to the first region of the inner stent;

a plurality of arms projecting laterally outward from the base and inclined in a direction away from the first region in a deployed state, each arm including a first portion coupled to the base and a second portion; and a fixation structure extending from the second portion of the arms, the fixation structure having a plurality of struts that define an annular engagement surface configured to press outwardly against a native annulus of a native heart valve;

wherein the first portion of each arm has a first flexibility and the second portion of each arm as a second flexibility, wherein the first flexibility is greater than the second flexibility.

13. The prosthetic heart valve device of claim 12, wherein each arm is a V-shaped arm unit having two struts coupled to the base, the two struts extending laterally away from each other from the base to the fixation structure, each of the two struts having the first portion with the first flexibility and the second portion with the second flexibility.

14. The prosthetic heart valve device of claim 13, wherein the first portion of each strut is serpentine.

15. The prosthetic heart valve device of claim 12, wherein each arm unit is a Y-shaped arm unit having a trunk coupled to the base and struts extending from the trunk to the fixation structure.

16. The prosthetic heart valve device of claim 15, wherein only the trunk is serpentine.

17. The prosthetic heart valve device of claim 12, wherein the first region is an outflow region of the inner stent and the second region is an inflow region of the inner stent.

18. A prosthetic heart valve device comprising:

an inner stent;

a prosthetic valve assembly disposed within and coupled to the inner stent;

an outer stent comprising a fixation structure configured to press against a native annulus of a native heart valve; and a plurality of arms connecting the outer stent to the inner stent, wherein each of the arms extends radially outward from the inner stent to the outer stent, each of the plurality of arms comprising:

a first end;

a second end;

a first portion adjacent the first end; and a second portion disposed between the first portion and the second end, wherein the first portion of each arm is a single strut and the second portion of each arm is two struts such that each arm is Y-shaped, wherein the first portion is a serpentine strut and the second portion is a non-serpentine strut.

19. The prosthetic heart valve device of claim 18, wherein the first end is coupled to the inner stent and the second end is coupled to the outer stent.

20. The prosthetic heart valve device of claim 18, wherein the non-serpentine strut is straighter than the serpentine strut.

* * * * *